United States Patent
Atanasoff et al.

(10) Patent No.: US 10,408,744 B2
(45) Date of Patent: Sep. 10, 2019

(54) SYSTEM AND METHOD FOR MONITORING ATOMIC ABSORPTION DURING A SURFACE MODIFICATION PROCESS

(71) Applicant: Accustrata, Inc., Rockville, MD (US)

(72) Inventors: George Atanasoff, Washington, DC (US); Christopher Metting, Rockville, MD (US); Hasso Von Bredow, McLean, VA (US)

(73) Assignee: Accustrata, Inc., Rockville, MD (US)

( * ) Notice: Subject to any disclaimer, the term of this patent is extended or adjusted under 35 U.S.C. 154(b) by 0 days.

(21) Appl. No.: 15/998,483

(22) Filed: Aug. 16, 2018

(65) Prior Publication Data

US 2018/0364156 A1 Dec. 20, 2018

Related U.S. Application Data

(63) Continuation of application No. PCT/US2016/018225, filed on Feb. 17, 2016.

(51) Int. Cl.
*G01N 21/31* (2006.01)
*H01J 37/32* (2006.01)
(Continued)

(52) U.S. Cl.
CPC ....... *G01N 21/3103* (2013.01); *C23C 14/547* (2013.01); *G01N 21/85* (2013.01);
(Continued)

(58) Field of Classification Search
CPC .......... H01L 21/67253; G01N 21/3103; G01N 21/31; G01N 2201/08; C23C 14/547; H01J 37/32972
(Continued)

(56) References Cited

U.S. PATENT DOCUMENTS

| 7,145,653 B1 | 12/2006 | Templeton et al. |
| 8,092,695 B2 | 1/2012 | Grimbergen |

(Continued)

FOREIGN PATENT DOCUMENTS

| AU | 2006200758 A1 | 3/2006 |
| EP | 1926125 A1 | 5/2008 |

OTHER PUBLICATIONS

Ray et al., "Improved optical scheme for nonintrusive vapor density monitoring by atomic absorption spectroscopy," J. Vac. Sci. Technol. A., Jul./Aug. 1998, 16(4):2345-2349.
(Continued)

*Primary Examiner* — Binh X Tran
(74) *Attorney, Agent, or Firm* — Womble Bond Dickinson (US) LLP

(57) ABSTRACT

A processing system monitors and/or controls a surface modification process occurring on a substrate within a processing chamber. An optical processing module having a light emission submodule to output a generated light signal and an optical detection submodule to detect a resultant light signal, is connected via fiber optic cables to light illuminating and light receiving components located within the chamber. A processor determines an amount of atomic absorption by an atomic element encountered by a probing beam passing between the illuminating and receiving components, based on the intensity of the generated light signal, the intensity of the received light signal and optionally the spontaneous emission of the atomic element in the absence of illumination by a probing beam. Based on the determined amount, the system derives a plurality of parameters of the modified substrate, their spatial and temporal uniformity, and information about process conditions in the processing chamber.

26 Claims, 12 Drawing Sheets

(51) Int. Cl.
*H01L 21/67* (2006.01)
*C23C 14/54* (2006.01)
*G01N 21/85* (2006.01)

(52) U.S. Cl.
CPC .. *H01J 37/32972* (2013.01); *H01L 21/67253* (2013.01); *G01N 2201/08* (2013.01)

(58) Field of Classification Search
USPC ..................................................... 216/59, 60
See application file for complete search history.

(56) References Cited

U.S. PATENT DOCUMENTS

| | | | | |
|---|---|---|---|---|
| 2015/0255262 A1* | 9/2015 | Murtazin | ............. | H01J 49/105 |
| | | | | 356/316 |
| 2015/0284763 A1* | 10/2015 | Rehse | ................. | G01N 21/718 |
| | | | | 435/34 |
| 2015/0284851 A1* | 10/2015 | Du | ....................... | C23C 14/544 |
| | | | | 427/10 |
| 2016/0025656 A1* | 1/2016 | Jevtic | ...................... | H05H 1/46 |
| | | | | 324/633 |
| 2018/0267086 A1* | 9/2018 | Rinzan | ................. | G01L 9/0072 |

OTHER PUBLICATIONS

International Preliminary Report on Patentability dated Dec. 11, 2018, issued in PCT counterpart application (No. PCT/US2016/018225).

\* cited by examiner

| States | State 1 | State 2 | State 3 | State 4 | State 5 | State 6 |
|---|---|---|---|---|---|---|
| Description | Dark Reference | Chamber Background Reference | Light Sources reference | Atomic emission measurement | Atomic absorption measurement | Component contamination reference |
| Components 208/209 | NA | Closed | NA | Open | Open | Closed |
| Component 214 | NA | Closed | Open | Closed | Open | Open |
| Component 216 | NA | NA | Pos. "1" | NA | Pos."2" | Pos. "2" |
| Component 225 | Pos. "5" | Alternate over all measurement channels "1","2","3"…. | Pos. "4" | Alternate over all measurement channels "1","2","3"…. | Alternate over all measurement channels "1","2","3"…. | Alternate over all measurement channels "1","2","3"…. |

SYSTEM AND METHOD FOR MONITORING ATOMIC ABSORPTION DURING A SURFACE MODIFICATION PROCESS

RELATED APPLICATIONS

This is a Bypass Continuation of International Patent application no. PCT/U2016/018225, filed 17 Feb. 2016 and published as WO 2017/142523A1 on 24 Aug. 2017. The contents of the aforementioned application, as amended in the Article 19 submission of 19 Jun. 2016 and further amended in the Article 34 submission of 11 Jul. 2018, are incorporated by reference in their entirety.

GOVERNMENT LICENSE RIGHTS

This invention was made with government support under DE-SC0013241 awarded by Department of Energy. The government has certain rights in the invention.

FIELD OF THE INVENTION

The present innovation generally relates to systems and methods for the monitoring and control of surface modification processes. More particularly, it relates to systems and methods employing atomic spectra for real-time monitoring and control of such parameters as momentary mass and thickness of the deposited or etched material, momentary deposition or etching rate, material phase and lattice structure of the films deposited or removed from a substrate via a vacuum-assisted process, as well as a variety of physical parameters of the modified surface and their uniformity, such as structural, mechanical, chemical and thermal properties.

BACKGROUND OF THE INVENTION

Many fabrication processes involve addition of layers or material to the surface of a specimen or subtraction of layers or material from the specimen to achieve desired optical, mechanical, electrical, electro-optical or any other physical feature that influences performance. Such processes are commonly known as surface modification processes. The surface on which the process occurs is commonly referred as a substrate. Surface modification processes have a wide range of applications including but not limited to material processing, semiconductor fabrication, energy generation and conversion devices, optical thin films, X-ray and UV optics, nanotechnology, meta-materials, general and 3D printing, etc. Surface properties such as roughness, relief, chemical homogeneity, uniformity and optical, electrical, thermal and mechanical properties can influence the properties or performance of the final device.

The process of thin film deposition is one example of an additive surface modification process. Thin films are thin material layers ranging from fractions of a nanometer to tens of microns in thickness. The substrate on which the thin films are formed (e.g., by deposition) can be a bare substrate, or may already have existing features. Various forms of physical vapor deposition (PVD) and chemical vapor deposition (CVD) are examples of thin film deposition processes. While most thin film deposition processes take place in vacuum, some processes may take place at atmospheric, or even higher, pressure conditions. The process usually consists of creating vapors of material by chemical of physical means such as plasma generation, evaporation, sputtering, sublimation or differential pressure and subsequent condensation of the vapors on the surface of the deposited substrate. Many other varieties of thin film deposition processes exist, such as implantation, laser-pulsed evaporation, atomic layer deposition, molecular epitaxy, spraying, thermal diffusion, surface oxidation, etc.

Thin film formation is a complex process requiring thorough control of the process parameters and, in some cases, control of film characteristics, such as optical, electrical, chemical composition, lattice orientation, thermal properties and mechanical stresses, while maintaining geometrically, stoichiometrically and structurally uniform films during film growth. Some of the materials that have been used to form thin films include amorphous and crystalline silicon, germanium, metal oxides, nitrides, carbides, other compound materials, a variety of semiconductors, dielectrics, metals, polymers, inks, toners and others. Thin-films are often deposited in multiple layers to achieve desired characteristics. In some cases, there is no definitive interface between separate layers as their properties gradually change from one layer to another. In other cases, the thickness and the properties of the layers are modulated, or vary in certain ways in the depth of the coating. Furthermore, the thickness and the properties of the layers can also be modulated or vary in all 2 or 3 dimensions as is the case in a variety of patterned coatings, general and 3D printing, MEMS, thin film microlenses, photonic crystals, waveguides, optical displays and many other optical products. Geometrical contact and shadow masks can be used to control the vapor distribution over the deposited substrate. A large variety of substrates can be used, including flexible substrates and substrates that can later be removed or etched away leaving the thin film coating to be self-supported, or to be transferred to another substrate.

Some other surface modification processes are caused by spontaneous means or by the environment at which the surface is exposed, such as ageing, corrosion, residue deposition, material fatigue, etc., and might need to be avoided or controlled in order to minimize their occurrence. Yet, some surface modification processes take place at the boundary between different solid and/or liquid materials, such as electro-chemical plating, Langmuir-Blodgett film formation, printing, plating, etc.

Subtractive surface modification processes are characterized by the intentional or unintentional removal of material from the substrate. As with the additive processes, there is a large variety of subtractive processes. One example of a subtractive surface modification process is surface etching. Etching is used in micro-fabrication to remove layers from the surface of a substrate (e.g., a wafer or another specimen). Etching, stripping, and laser ablation are precise processes which require strict control of the process parameters in order to achieve the desired etching rate, etching profile and selectivity. In the ion etching process, control of the ratio of ion/reactive components in the plasma offers a convenient means to control the etching rate, the etching profile and selectivity. Another convenient means to control the process is achieved by applying bias voltages with different magnitude, profiles, waveforms, etc. Geometrical contact and shadow masks are often used to control the profile of layer subtraction from the substrate.

Another example of a subtractive surface modification process is the layer removal by mechanical scribing, such as grinding, polishing or spontaneous surface wear.

Surface modification processes typically change over time in an unwanted manner (i.e., randomly or systematically vary or fluctuate), causing the modified surface or specimen to either gradually deviate from the target values or otherwise unpredictably change.

One reason for unwanted change in the process is the gradual overcoating of the processing chamber walls during the process, causing unwanted change in the thermal, optical or electrical properties inside the chamber. For example, deposition of a dielectric layer on the chamber walls during a process may gradually change the electrical conductivity and/or electro-isolation properties of the surrounding area of the process, the reflective properties of the walls or create temperature gradients that gradually affect the quality of the thin film. Another typical example of unwanted change in the process parameters is the erosion of the sputtering target as material is removed from it, causing non-uniformity of the thickness, the chemical composition and other parameters of the deposited film.

During the last several decades, the significance and complexity of surface modification processes have been accelerating. For example, the new generation semiconductor processes bring tremendous performance advantages, but also come with new challenges associated with process accuracy and adequate process control. The new generation surface modification processes struggle with problems resulting from the lack or delay in adoption of adequate, dynamic process control capability. The current state-of-the-art process control is predominantly "after-the-fact", based on "snapshot" metrology and run-to-run control.

The most important process control challenges that must be overcome to make the next generation thin film processes more efficient and reduce waste are the in-situ monitoring and the control of:

Extremely thin films (with thickness below 40-50 angstroms); Such thin films cannot be controlled reliably by using legacy quartz crystal monitoring, nor optically due to the lack of measurable interference fringes in the UV and visible light;

Very thick layers or multilayer stacks (with thickness over 20 μm); Such thick films and coatings also cannot be controlled by quartz crystal monitoring due to the limited amount of material that can be deposited on one or limited number of quartz chips, nor optically, due to the multitude of very sharp and dense optical interference fringes;

Compound thin films and materials. These are composed of two or more elements from different groups of the periodic table. Compound thin films and materials have a very broad use such as semiconductor and material processing technology, linear and non-linear optics, X-Ray technology, electronics, lighting, solar, superconductors, thermal and/or diffusion coatings, catalysts, bond coatings, variety of cladding materials, etc. Their chemical composition is critical for the material properties. For example control of composition of InGaN thin film quantum wells for the light emitting diodes used in the solid-state lighting industry requires accuracy better than 0.1 at. %. In-situ composition control during the process of compound material deposition is a critical enabling technology for the introduction of compound materials into daily life.

Structured 2-3D-pattern films (nanostructures, MEMS, photonic band-gap structures, thin film micro-lenses);

Special property or special profile films (metallic, absorbing, non-linear, porous, anisotropic, quintic, grad-index, etc.);

Thin film processes with very fast deposition rates (>2-5 nm/sec);

Thin films deposited on non-flat substrates or samples with odd geometries;

Insufficient process control capabilities always result in increased product cost, due to the inherent waste of energy, material, labor and intellectual effort and delays the deployment of many important technologies. The problem becomes even more significant as the new-generation of thin film products become increasingly complex. Furthermore, in most cases both the thin film products and the deposition equipment itself are "over-engineered" to meet even tighter product specifications. For example, vacuum chambers are frequently designed larger and coatings are "overdesigned" to ensure that, despite process deviations and inaccuracies, the production will still achieve acceptable uniformity, repeatability and yield. Also, the "over-engineering" affects process scalability, time-to-market and significantly contributes to waste and inflated product cost.

Most of today's thin-film thickness monitors and deposition rate controllers implement the quartz crystal microbalance and/or photometric method of metrology. The quartz crystal monitoring (QCM) is only sensitive to the mass of the deposited film material, and cannot provide important information about the film quality, such as film composition or structure. The instrumentation is very sensitive to process temperature, temperature gradients and requires water-cooled sensors inside the vacuum chambers. Furthermore, the measured results are very sensitive to the sensor's position inside the chamber and require thorough calibration and calculation of tooling factors, specific to each deposited material. Still, the uncertainty in the QCM readout is relatively high. QCM is not practical for many applications (such as the sputtering of compound targets or alloys, ion implantation or etching).

Interferometric monitoring of multi-layers during deposition, frequently referred to as "optical monitoring" or OMS, (including monitoring reflectance, transmittance or both, at normal or oblique incidence) has other limitations. These methods are only applicable to 1) transparent films, 2) films having sufficient optical thickness to display measurable interference patterns in the visible spectrum, 3) multi-layer stacks with total thickness not exceeding 5-10 μm, and 4) frequently requires equipment refurbishing. Some other solutions, such as in situ ellipsometry, RHEED, X-Ray scattering, electron diffraction and fluorescence methods are used in R&D laboratories for in situ film characterization, but require complicated theoretical fitting to retrieve actionable information. For instance, the in situ ellipsometry, frequently used in R&D settings, is slow in fitting the measured data to established models, requires very thorough calibration, expert data interpretation and can involve costly deposition chamber refurbishing. As a result, it has made little penetration as an in situ process control tool on the manufacturing floors.

Atomic Absorption Spectroscopy (AAS) is a promising method for accurately determining the deposition rate by correlating the atomic flux density in the vicinity of the substrate under deposition to the attained film thickness. Being independent from the film growing on the substrate or substrate characteristics, this technique is ideal for monitoring extremely thin and opaque films at a wide range of deposition rates, as well as compound thin films and complex substrate shapes. It does not shadow the deposition cloud and is much easier to calibrate than the QCM. As a result, in situ AAS can resolve most of the problems identified above.

AAS relies on the selective absorption of photons by the free atoms in the plasma surrounding the deposited substrate and follows the Beer-Lambert law. The electrons of the atoms can be promoted to more energetic states for a short period of time by absorbing a defined quantity of energy (electromagnetic radiation of a given spectral linewidth). This amount of energy is specific to a particular electron transition in a particular atomic element. The radiation flux through the atomic region is measured both without and with a sample present using a detector, and the ratio between the two values (absorption) is converted to detect the presence or analyze the amount of atoms (i.e. atomic concentration or mass). The measured absorption value is proportional to the atom flux density and can be used to derive calibration functions related to the rate of deposition or etching of the substrate or other physical parameters of the modified layers. Typically, AAS uses specific wavelengths of UV light that correspond to the specific absorption spectra of the element being monitored. The absorption lines are typically very narrow (referred as spectral linewidths) and lie mostly in the DUV and UV spectrum. The light sources are typically hollow cathode lamp sources (HCL) with a cathode that is identical to the element that is monitored. Multi-element HCL sources with 2-3 elements are also available.

FIG. 1 is a functional block diagram of the prior art ACCUFLUX® in-situ atomic absorption spectroscopy thin film process monitoring system marketed by SVT Associates in Eden Prairie, Minn. The thin film deposition chamber 101 comprises a substrate holder 102, which can have a variety of shapes and can perform different movements during deposition such as simple rotation, planetary rotation, translational movement or others. The substrate holder 102 can support one or more substrates 103 arranged in variety of configurations such as circular, rectangular or others. The material vapor cloud (i.e. plasma) that forms a deposition region 104 is directed towards the substrate by a deposition source 105 or multiple sources as per the materials to be deposited on the substrate. A person skilled in the art recognizes that multiple deposition configurations (vertical, horizontal, up-down, down-up, etc.) and variety of processes (physical, chemical, reactive, ablative, implantive, radiative, etc.) exist, which can all be represented by the configuration illustrated in FIG. 1.

The in-situ atomic absorption spectroscopy system is installed outside the processing chamber and generically consists of element-specific hollow cathode light sources 109 that contain the atomic elements identical to the atomic elements that are measured, beam shaping optics (i.e. focusing lenses) 110 focusing the beam inside the deposition region 104 in the chamber 101 through a tube 111, which is installed on the first optical viewport 112 of the processing chamber 101. The beam is split into two beams by an optical beam splitter 113. One of the beams is directed through an aperture 114 for power reference (referencing beam) and the second beam is directed to the processing chamber 101 for plasma measurement (probing beam). The reference and the probing beams are filtered by a mechanical chopper with a filter 115 and directed to the optical detector 116 (i.e. photomultiplier tube) by means of a focusing or other beam shaping optics 110. The probing beam enters the processing chamber through the first optical viewport 112 installed on the chamber walls, traces the deposition region 104, leaves the processing chamber through a second optical viewport 117 on the opposite wall of the processing chamber and is reflected back into the second optical viewport 117 by the beam retro-reflector 118. It again enters the processing chamber through the second optical viewport 117 and probes the deposition region 104 for a second time before it leaves through the first optical viewport 112. Once back from the measurement, the probing beam is reflected by the beam splitter 113 to the mechanical chopper 115 and to the photodetector 116 though the focusing optics 110.

The computer 106 processes and displays the measurement information to the operator. Optionally, 106 can communicate to the processing chamber through one or more controllers 107, which may control a variety of sub-systems such as mechanical shutters 108, deposition sources 105, vacuum pumps, heaters, substrate rotations, etc. as well as a variety of process parameters such as gas flow, bias voltage, temperature, etc. In some cases 106 and 107 might be integrated into one computer system.

This configuration of AAS monitoring system uses UV-transparent optical ports for the incident and the reflected beam, mechanical modulation (chopper) and a photo-multiplier or other optical detector. The probe beam travels not only over the substrate area, but also travels considerable distances L1 and L2 between the substrate and the chamber walls.

U.S. Pat. No. 8,541,741 discloses a bench-top AAS system, in which no deposition chamber is used. However, AAS measurements are made with the assistance of optical fibers for transmitting and receiving signals.

SUMMARY OF THE INVENTION

The subject matter of the present application relates to an in-situ atomic spectroscopy system and method for monitoring and control of a surface modification process, and also an assembly of components and/or methods for modifying a processing chamber to have atomic spectroscopy capabilities.

In a first aspect, the subject matter of the present application is directed to a processing system comprising a processing chamber having a substrate holder for holding at least one substrate and a process region, the processing system configured to monitor and/or control a modification process occurring on the substrate, the processing system further comprising:

at least one illuminating optical component mounted within the processing chamber and configured to receive at least one generated light signal and direct at least one probing beam through the process region without intersecting the substrate, in response thereto;

at least one corresponding receiving optical component mounted within the processing chamber and configured to receive said at least one probing beam after it has passed through the process region, and output at least one resultant light signal in response thereto, the at least one resultant light signal being reflective of an amount of atomic absorption by at least one element of interest in the process region;

an optical processing module comprising:
  a light emission sub-module configured to output the at least one generated light signal, which is received by said at least one illuminating optical component; and
  an optical detection sub-module configured to receive said at least one resultant light signal from the at least one receiving optical component;

a processor coupled to at least the optical detection submodule and configured to determine, based on said at least one resultant light signal, an amount of said at least one atomic element of interest in the process region.

In a second aspect, the subject matter of the present application is directed to a method for in-situ monitoring and/or control of a surface modification process occurring on a substrate in a processing chamber, the processing chamber having a particle source therein and a process region between the particle source and the substrate. The method comprises: (a) providing a generated light signal into the processing chamber, via a first fiber optic cable extending from outside the processing chamber to inside the processing chamber; (b) based on the generated light signal, directing at least one probing beam through the process region, without intersecting the substrate; (c) receiving said at least one probing beam within the processing chamber after it has passed through said process region; (d) in response to receiving said at least one probing beam, outputting at least one resultant light signal via a second fiber optic cable extending from inside the processing chamber to outside the processing chamber, the at least one resultant light signal being reflective of an amount of atomic absorption by at least one element of interest in the process region; and (e) based on the at least one resultant light signal, determining an amount of said at least one atomic element of interest in the process region.

In a third aspect, the subject matter of the present application contemplates providing a collection of components and computer software, or a "kit", for modifying a processing chamber of the sort configured to carry out a surface modification process on a substrate located therein, so that an amount of at least one element of interest within a process region within the chamber can be determined using optical components mounted within the chamber itself. The kit includes (a) an optical processing module comprising a light emission sub-module and an optical detection sub-module; (b) at least one illuminating optical component for installation inside the processing chamber; (c) a first optical fiber to connect the optical processing sub-module to the at least one illuminating optical component, when the illuminating optical component is installed inside the processing chamber; (d) at least one receiving optical component for installation inside the processing chamber; (e) a second optical fiber to connect the optical processing sub-module to the at least one receiving optical component, when the receiving optical component is installed inside the processing chamber; and (f) software, which when executed on a processor coupled to the optical processing module, is configured to: (i) cause the light emission sub-module to output a generated light signal; (ii) cause the optical detection sub-module to detect a resultant light signal in response to the generated light signal, the resultant light signal being reflective of an amount of atomic absorption by at least one element of interest in the process region; and (iii) based on said resultant light signal, determine an amount of said at least one atomic element of interest in the process region.

The kit's software, when executed, may further be configured to compensate for a spontaneous atomic emission component of the resultant light signal, when determining the amount of said at least one atomic element of interest in the process region.

The kit may include a fiber optic component holder (FOCH) having the least one illuminating optical component mounted on a first portion thereof, and having the at least one receiving optical component mounted on a second portion thereof, wherein: the receiving optical component is optically aligned with the illuminating optical component and spaced apart therefrom by an optical path length L3. The FOCH may be loop-shaped though other configurations are contemplated as well.

In the FOCH, the optical path length L3 may no greater than 140% of a substrate length L0, measured in a direction between the two optical components, of a substrate accommodated in the processing chamber.

In a fourth aspect, the subject matter of the present application contemplates a method of modifying a processing chamber of the sort configured to carry out a surface modification process on a substrate located therein, so that an amount of at least one element of interest within a process region within the chamber can be determined using optical components mounted within the chamber itself. The method comprises: (a) providing an optical processing module comprising a light emission sub-module and an optical detection sub-module; (b) installing at least one illuminating optical component in the processing chamber, the at least one illuminating optical component being connected via optical fiber to the light emission sub-module; (c) installing at least one receiving optical component in the processing chamber, the at least one receiving optical component being connected via optical fiber to the optical detection sub-module; and (d) installing software on a computer coupled to the optical processing module, the software when executed, being configured to: (i) cause the light emission sub-module to output a generated light signal; (ii) cause the optical detection sub-module to detect a resultant light signal in response to the generated light signal, the resultant light signal being reflective of an amount of atomic absorption by at least one element of interest in the process region; and (iii) based on said resultant light signal, determine an amount of said at least one atomic element of interest in the process region.

The method of modifying may include installing software, which when executed, compensates for a spontaneous atomic emission component of the resultant light signal, when determining the amount of said at least one atomic element of interest in the process region.

The method of modifying may additionally include installing a fiber optic component holder (FOCH) in the processing chamber, the FOCH having the least one illuminating optical component mounted on a first portion thereof, and having the at least one receiving optical component mounted on a second portion thereof, wherein: the receiving optical component is optically aligned with the illuminating optical component and spaced apart therefrom by an optical path length L3; and the optical path length L3 is no greater than 140% of a substrate length L0, measured in a direction between the two optical components, of a substrate accommodated in the processing chamber.

In a fifth aspect, the subject matter of the present application is directed to a processing system comprising a processing chamber having a substrate holder for holding at least one substrate, the processing chamber having a particle source therein and a process region between the particle source and the substrate. The processing system further comprises (a) at least one receiving optical component mounted within the processing chamber on a first side of the substrate, the receiving optical component configured to receive emitted light from an element of interest present in the process region, and output a resultant signal in response thereto, the emitted light being within a finite spectral linewidth corresponding to said element of interest; (b) at least one light blocking optical component mounted within the processing chamber on an opposite second side of the substrate, the light blocking optical component being optically aligned with the receiving optical component and spaced apart therefrom by an optical path length L3; (c) an optical detection processing module comprising: (i) an optical detection sub-module configured to receive said at least one resultant light signal from the at least one receiving optical component; and (d) a processor coupled to at least the optical detection sub-module and configured to determine, from said at least one resultant light signal, an amount of spontaneous atomic emission of said element of interest. The optical path length L3 is no greater than 140% of a substrate length L0 measured in a direction between the receiving optical component and the light blocking component.

It will be understood that the above-said is a summary of the subject matter of the present application, and that the various systems and method summarized above may further comprise any of the features described herein below. Specifically, the following features, either alone or in combination, may be applicable to any of the above aspects, be it the processing system, method of operation, a kit, or method of modifying a processing chamber:

(i) The resultant light signal may be reflective of a combined amount of atomic absorption and spontaneous atomic emission, the latter being the atomic emission in the absence of illumination by a probing beam. In such case, the processor, method and/or software when executed, may compensate for a spontaneous atomic emission component of the resultant light signal, when determining the amount of said at least one atomic element of interest in the process region.

(ii) At least one fiber optic component holder (FOCH) may be mounted within the processing chamber, and the illuminating optical component and its corresponding receiving optical component are both mounted on said at least one fiber optic component holder.

(iii) The FOCH may be loop-shaped.

(iv) The illuminating optical component and its corresponding receiving optical component may be mounted within the processing chamber such that an optical path length L3 separating the illuminating optical component from its corresponding receiving optical component, is no greater than 140% of a substrate length L0 measured in a direction between the two optical components.

(v) A first distance L1 between the illuminating optical component and a first edge of the substrate may be less than 50 mm; a second distance L2 between the receiving optical component and a second edge of the substrate may be less than 50 mm; and a height H separating the probing beam from the substrate, may be less than 30 mm.

(vi) A plurality of illuminating optical components may be provided, each illuminating optical component configured to direct at least one probing beam in the direction of a corresponding receiving optical element.

(vii) In a plan view of the component holder and substrate holder, the probing beams may not intersect one another; and/or at least two of the illuminating and receiving optical components are located at different heights, relative to the substrate.

(viii) At least one of the illuminating and receiving optical components additionally serves as one or more of a beam collimator, a focuser, a polarizer, an optical filter and a mirror.

(ix) At least one reflective component may be positioned within the processing chamber to reflect the probing beam after it has passed through the process region, such that the probing beam passes a second time through the process region prior to being received by a receiving component and the at least one resultant light signal being outputted. In such case, the probing beam may be directed in a way to be received by the corresponding receiving element.

(x) A plurality of atomic elements of interest may be present in the process region, in which case, the light emission submodule is configured to generate a plurality of element-specific spectral linewidths, with at least one element-specific spectral linewidth corresponding to each of said plurality of elements of interest; the at least one resultant light signal comprises spectral information corresponding to said plurality of element-specific spectral linewidths; and the processor is configured to determine an amount of each of said plurality of elements of interest present in the process region.

(xi) The light emission sub-module may be configured to generate a plurality of element-specific spectral linewidths for a single atomic element of interest present in the process region, in which case, the at least one resultant light signal comprises spectral information corresponding to said plurality of element-specific spectral linewidths for that single atomic element; and the processor is configured to determine an amount of said single atomic element of interest in the process region, based on spectral information corresponding to said plurality of element-specific spectral linewidths.

(xii) Based on a plurality of determined amounts of said at least one atomic element of interest in the process region over time, one or more of the following may be determined: a momentary mass, a momentary thickness, a deposition rate, an etching rate, an etching selectivity, an etching profile, a chemical composition, a phase, a crystal lattice and a microstructure, of a thin film being modified on the substrate surface.

(xiii) Based on the generated light signal, a plurality of probing beams may be directed to pass through different portions of said process region, to thereby form a corresponding plurality of resultant light signals; and based on said plurality of resultant light signals passing through different portions of said process region, a spatial distribution of at least one of said momentary thickness, said deposition rate, said etching rate, said etching selectivity, said etching profile, said chemical composition, said phase, said crystal lattice and said microstructure of a thin film being modified on the substrate surface, may be determined.

(xiv) Based on the generated light signal, a plurality of probing beams may be directed to pass through said process region at different times, to thereby form a corresponding plurality of resultant light signals separated in time; and based on said plurality of resultant light signals passing through said process region at different times, a temporal distribution of at least one of said momentary thickness, said deposition rate, said etching rate, said etching selectivity, said etching profile, said chemical composition, said phase, said crystal lattice and said microstructure of a thin film being modified on the substrate surface, may be determined.

(xv) Based on a plurality of determined amounts of said at least one atomic element of interest in the process region over time, one or more of the following processing conditions of a processing chamber may be controlled, such as an operation setpoint of a particle source within the processing chamber, gas flow rates of the gases introduced into the processing chamber, a precursor gas conditions, a temperature setpoint inside the processing chamber, a pressure setpoint in the processing chamber, and a bias voltage applied to the components of the processing chamber.

(xvi) The processor and/or the controller may control one or more of the aforementioned processing conditions of a processing chamber without human intervention.

(xvii) The processing chamber may comprise a plurality of chamber compartments; and the substrate holder and its associated FOCH are configured to move together in the processing chamber and enter different chamber compartments.

(xviii) The processing chamber may comprise a plurality of chamber compartments or process areas, at least two of the chamber compartments or process areas having at least one FOCH located therein, in which case the substrate holder is configured to undergo translational movement in the processing chamber and enter different chamber compartments or process areas.

(xix) Multiple probing beams with different configurations may trace a deposition region in the vicinity of the modified substrate and derive spatial information about the vapor distribution over the deposited substrate.

(xx) The FOCH with the fiber optics components may be installed directly on the substrate holder and moves with the substrate holder inside the deposition chamber, in its compartments or in separate deposition chambers, as is the case for a cluster tool, deposition line or other set of complex surface processing equipment.

(xxi) Optical spectrometers and monochromators can be used as spectral dispersive components in order to detect and process the resultant light signal.

(xxii) Constant referencing of the light source power, the power of the probing beam, the intensity of the spontaneous atomic emission and the background reference may be performed during one duty cycle.

(xxiii) Based on the generated light signal, a plurality of probing beams may be directed to pass through different portions of said process region, to thereby form a corresponding plurality of resultant light signals; and based on said plurality of resultant light signals, a spatial distribution of an amount of said at least one atomic element of interest in the process region may be determined.

(xxiv) Based on the generated light signal, a plurality of probing beams may be directed to pass through different portions of said process region at different times, to thereby form a corresponding plurality of resultant light signals separated in time; and based on said plurality of resultant light signals separated in time, a temporal distribution of said at least one atomic element of interest in the process region may be determined.

(xxv) An optical path length L3 of the probing beam between said directing step and said receiving step, may be no greater than 140% of a substrate length L0 measured in the direction traveled by the probing beam.

(xxvi) The probing beam may be reflected at least once after it has passed through said process region, such that the probing beam passes through a different portion of said process region prior to being received and the at least one resultant light signal being outputted.

(xxvii) A generated light signal comprising a plurality of element-specific spectral linewidths may be generated, each spectral linewidth corresponding to a specific absorption or emission peak of a single atomic element of interest. A resultant light signal comprising a corresponding plurality of element-specific spectral linewidths may then be generated; and an amount of said single atomic element of interest in the process region may be determined, based on spectral information corresponding to said plurality of element-specific spectral linewidths.

(xxviii) A plurality of atomic elements of interest may be present in the process region, in which case a generated light signal comprising a plurality of element-specific spectral linewidths may be generated, each element-specific spectral linewidth corresponding to a single absorption or emission peak of each of a corresponding plurality of different atomic elements of interest. A resultant light signal comprising a corresponding plurality of element-specific spectral linewidths may then be generated, and an amount of each of said plurality of elements of interest present in the process region may be determined.

(xxix) The surface modification process may be changed, without human intervention, in response to determining said amount of said at least one atomic element of interest in the process region.

BRIEF DESCRIPTION OF THE DRAWINGS

FIG. 3 depicts the operational state diagram of the embodiment shown in FIG. 2.

DETAILED DESCRIPTION OF THE DRAWINGS

Figure 2:
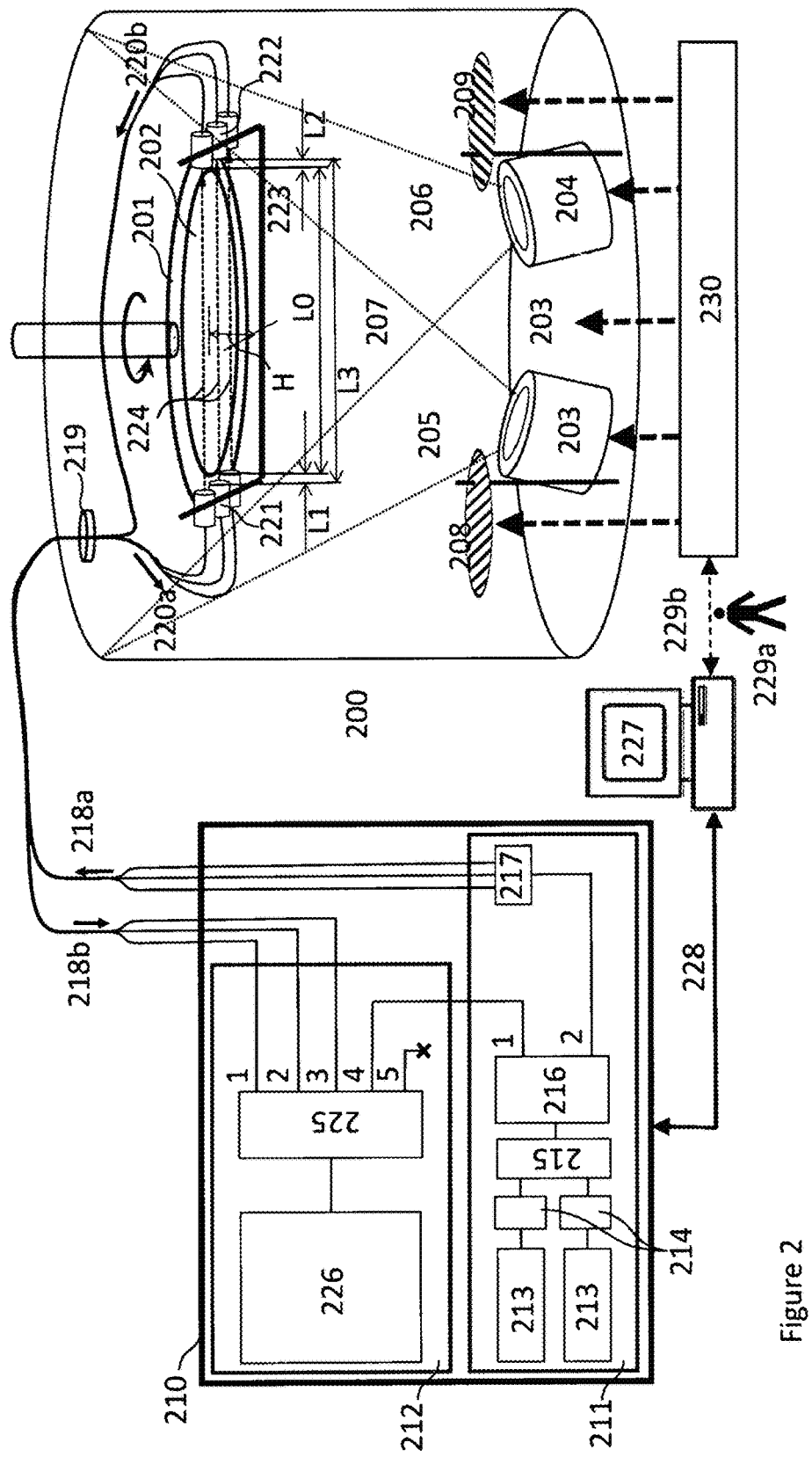
FIG. 2 is a functional block diagram of one embodiment of a system in accordance with the current invention.

FIG. 2 is a functional block diagram of one embodiment of the present invention.

The processing chamber 200 includes a substrate holder 201, which supports one or more substrates 202 arranged in circular, rectangular or other configurations. The substrates 202 can have variety of forms and shapes and can be stationary or perform circular, planetary or another rotation, translational or another movement. The substrates 202 can also have pre-modified surfaces such as cleaned, polished, etched, deposited, patterned, as well as a variety of shapes and geometries such as flat, spherical or more complex. The processing chamber 200 has one or more sources of particles (two are shown) 203 and 204. These can be sources of deposition material particles generated from the source itself; thermal evaporators, effusion cells, magnetron, arc or ion beam sources, differential pressure sources, etc. In these cases the particle sources 203 and 204 form particle vapor clouds 205 and 206, which are directed towards the substrate 202. Sources 203 and 204 can also be indirect sources of particles, such as ion bombardment or radiation sources, which stimulate particle generation from the substrate itself.

Yet, in some cases sources 203 and 204 can stimulate secondary interactions between particles in the process region 207, surrounding the substrate 202. A person skilled in the art recognizes that a large variety of material sources used to generate or otherwise form a particle cloud in the process region 207 exist or can be devised in the future.

The process region 207 is a volume in the vicinity of the substrate 202, which comprises the material particles resulting from the operation of sources 203 and 204 and/or from the interaction of these particles with the materials of the substrate. The process region 207 can include neutral or ionized atomic, molecular, cluster or oligomer particles and combinations of such. Particles can be directed to the substrate 202 by means such as kinetic energy of the particles. Particles can be extracted from the substrate by means such as ablation or sublimation, or can be formed in the process region 207 by means such as secondary interactions between other particles.

The material particles in the process region 207 can be deposited on the substrate to form a single layer or multi-layers of material by physical condensation or another deposition mechanism. The layers comprise a single chemical element or combinations of multiple elements, forming a metallic, dielectric, semi-conductive, organic, biological or another compound or mixed substance. Single layers and multilayers can be formed on the substrate as solid or liquid substances and/or exist in any of these two forms after their deposition.

In other cases, the sources of particles 203 and 204 form clouds of energetic or ionized particles (i.e. partially or fully ionized), which remove material from the substrate 202 instead of depositing it, such as in the case of ion etching. In such cases the process region 207 contains material particles from the eroded substrate.

In other cases, the processing region 207 can include particles that can physically penetrate in the substrate, such as ion implantation, or modify the surface properties of the substrate, such as surface cleaning, surface hardening or polishing.

Yet in other cases the sources 203 and 204 may generate material vapors or electromagnetic radiation, which interacts with the substrate 202 or other particles, forming residual materials or particles in the processing region 207. Examples of such processes are the laser ablation, laser melting, surface alloying or radiation surface treatment. In such cases the processing region 207 may contain residual particles from the interaction process with the substrate, or particles formed during the secondary interaction in the region 207.

A person skilled in the art recognizes that multiple deposition configurations (vertical, horizontal, up-down, down up, etc.) and variety of processes (physical, chemical, reactive, sputtering, evaporation, sublimation, ablation, implantation, differential pressure, etc.) exist, which can be represented by the configuration, summarized on FIG. 2.

Mechanical or electronic actuating devices 208 and 209 such as valves, orifice closures, shutters, doors, masks, on-off switches or software-controlled devices are used to enable, disable or shape the formation of the particle clouds 205 and 206 and control the process region 207.

The processing chamber is controlled by one or more chamber controllers 230; however, processing chambers may exist that are controlled manually by an operator. The chamber controllers 230 may control a variety of sub-systems and process parameters, such as the material sources 203 and 204, actuating devices 208 and 209, vacuum pumps, heaters, substrate rotations, bias voltages. The system computer 227 processes and displays information to the operator 229a, and/or directly communicates to the controllers 230 through an electronic connection 229b. In some cases 227 and 230 can be integrated into one computer system. It is understood, however, that a programmable "processor" is associated with computer 227 and/or controller 230, and executes instructions in a known manner.

The in-situ atomic spectroscopy system as per the present embodiment includes three main components 1) an optical processing module 210, which is installed outside the processing chamber 200, 2) a fiber optics component holder 223, which supports the optical components 221 and 222 and is installed inside the processing chamber 200, and 3) a variety of optical fibers, or fiber bundles for guiding the light to and/or from the processing chamber 218a, 218b, 221a, 220b.

The component holder 223 is designed to hold and keep the optical components 221 and 222 in an optically aligned position inside the processing chamber. The components 221, 222 are held in a predetermined spaced relationship at known distances relative to one another. The component holder 223 can be a plug-and-play solution, which is used to configure, optically align and fix components 221 and 223 in place before delivery and installation at the user's process equipment. Care is taken to protect the components against thermal misalignment and contamination during processing, as well as to keep all components and fibers compact for easy re-configuration, service and maintenance.

The component holder 223 can have a variety of shapes. In one embodiment, the component holder 223 comprises a loop-shaped frame on which various optical components may be mounted. The loop-shaped frame may have a circular, rectangular, octagonal or other shape which may not even be a standard geometric shape. To ensure that components mounted on the loop-shaped frame maintain their positions relative to one another, the frame is preferably rigid and resistant to torsional forces and thermal deformation. In other embodiments, the component holder may be in the form of a bracket or other fixture to fit different chamber geometries, applications and user preferences. The component holder may instead comprise a plurality of separate portions, which are positioned in predetermined locations in the chamber. Regardless of its shape and configuration, the component holder is installed inside the processing chamber 200. This may be done by attachment to the chamber walls, or directly to one or more of the vacuum feedthroughs, such as the fiber optics feedthrough 219. In some embodiments, it may even be mounted to the substrate holder.

The optical processing module 210 generically comprises two major sub-modules: a light emission sub-module 211 and optical detection sub-module 212, which are defined functionally but may not be separated physically.

The light emission sub-module 211 generically comprises one or more light sources 213, light selecting, shaping and combining components 214 and 215 and light distribution components 216 and 217.

According to the first embodiment of the present invention, light sources 213 are element specific hollow cathode light (HCL) sources with cathodes, containing the chemical elements identical to the elements that are measured in the process region 207. Single element or multi-element HCL sources can be used to measure particles of a single or multiple elements in the process region 207 separately in time or simultaneously.

According to the second embodiment of the present invention light sources 213 are single or multiple fixed-wavelength or tunable light sources such as broadband or supercontinuum light sources with monochromators, tunable or fixed wavelength lasers or laser diodes.

Component 214 and 215 comprise two different or one consolidated single component used to select and combine light as well as shape the optical beams from the light sources 213. Component 214 comprises individual mechanical or electronic actuators (shutters), or a single multi-position shutter, used to select individual light sources, make combinations of them, or block them altogether. Component 215 combines the individual beams into a single beam, and can be constructed of several sub-components such as fiber optics or bulk-optics couplers, beam combiners or optical switches. Component 215 may also include a variety of sub-components such as focusing lenses, collimators, optical filters, light diffusers, beam homogenizers, polarization scramblers, etc. Also, components 214 and 215 can be arranged in reverse order, where 215 is interposed between the light source(s) 213 and component 214.

Light distribution component 216 and 217 comprise two different or one consolidated single component used to distribute light between different optical fibers. The primary fiber optics distribution component 216 directs the light between two or more fibers or fiber bundles, marked as positions "1" and "2". Other positions can be added as necessary. Light from position "1" is sent to a secondary distribution component 225 and to the optical detector 226 for light power reference. Light from position "2" is sent to a secondary distribution component 217 and distributed into different measurement channels used for measurement of the process region 207 (for illustrative purpose only 3 measurement channels are shown).

In one embodiment of the present invention, component 216 is a fiber optics 1×N switch, which consolidates the functions of both 216 and 217 and switches between positions "1" and "2". Position "1" comprises a fiber or fiber bundle, which is sent to a secondary distribution component 225 and to the optical detector 226 for light power reference. Position "2" comprises a fiber bundle with multiple measurement fibers illuminated simultaneously, or individual measurement fibers or fiber bundles, illuminated sequentially. In the last case position "2" can be a consolidated position comprising several positions, not shown in FIG. 2 for simplicity. Also, for illustration purposes only, position "2" shows only 3 measurement fibers or fiber bundles to support 3 measurement channels. It may include any number of measurement fibers to support one or more measurement channels.

In another embodiment of the present invention components 215 and 216 are combined in a single 2×N optical switch.

Yet, in another embodiment of the present invention all components 214, 215, 216 and 217 are combined in a single M×N optical Add/Drop switching component and consolidate all the described functions.

The optical detection sub-module 212 comprises fiber distribution component 225 and detector component 226.

According to one embodiment of the present invention component 225 is a 1×N optical switch, having multiple positions illustrated as positions "1-5". Any of these 5 positions can be a consolidated position comprising several positions, not shown in FIG. 2 for simplicity. When switched to positions "1", "2", "3" (or any number of positions corresponding to the amount of measurement channels) it selects and sends to the detector component 226 the light from the measurements in the process area 207. When switched to position "4" it sends to the detector 226 light collected directly from the light sources 213 for light power reference (i.e. HCL power reference). Position "5" is used to perform "dark" reference of the detector 226.

The detector 226 is built based on a variety of optical measurement techniques such as a photodetector with an optical filter, a monochromator with a photomultiplier tube, a CCD spectrometer or others. Persons skilled in the art may recognize the variety of available optical detecting and measurement solutions.

According to one embodiment of the present invention component 225 and 226 are combined into a single component, such as a single block of spectrometers cascaded together and operated by a single controller.

According to a second embodiment, component 225 is eliminated altogether and the light from the individual fibers or fiber bundles is sent to separate optical detectors, such as separate spectrometers, each controlled individually.

Yet, according to a third embodiment, position "5" of component 225 is eliminated and the "dark" reference is performed by configuring component 216 to position "2" and component 225 to position "4".

The individual fibers or bundles from component 217 are combined into one or more fiber optics cables 218. They enter the processing chamber 200 through one or more fiber optics feedthroughs 219. Using incoming light fibers 220a, the light is coupled into one or more illumination components 221, which are optically aligned with the corresponding receiving components 222 and fixed to the fiber optics component holder 223 installed in the process region.

Components 221 and 222 can provide one or more optical functions, and thus may additionally serve as beam collimators, focusers, polarizers, optical filters, mirrors or combinations of different components. In the embodiment in FIG. 2 they are marked as illumination and receiving components, respectively, in order to differentiate their functionality.

A single holder 223 can accommodate a variety of component configurations. The functionality of the components 221 and 222 can be configured both through configuring fibers 218a and 218b inside the module 210 and/or through configuring the components directly on the component holder. For example:

(a) components 221 and 222 can have the same optical design; e.g., they may both be fiber optics collimators;

(b) either or both components 221 and 222 can be configured to operate as an illumination component, receiving component or both;

(c) either or both components 221 and 222 can operate as an illumination and receiving component simultaneously by attaching both fibers 218a and 218b to a single component;

(d) either or both components 221 and 222 functionally represent only receiving components, operating simultaneously or sequentially;

(e) either or both components 221 and 222 can be a receiving component and simultaneously or sequentially act as a light-blocking component for another component with which they are optically aligned;

(f) either or both components 221 and/or 222 can be a reflector, reflecting the probing beam to another component, which may be also a reflector or a receiving component.

Three illumination and receiving components are shown for illustration only; however, any number of illumination or receiving components can be used to form one or more measurement channels. The position of the components 221 and 222, relative to the substrate 202, are characterized by distances L0, L1, L2, L3 and H. L0 is the length of the substrate area or region of interest, in a particular direction. L1 and L2 are the distances between the edge of the substrate or the edge of region of interest for measurement and the illumination 221 and receiving components 222, respectively. H is the vertical offset from the substrate to the path of the probing beam 224. Finally, the optical path length L3 is the total distance between the illumination and receiving components 221, 222.

Generally speaking, in the case of a planar substrate 202 retained on a planar substrate holder, the light beam's path length over the substrate 202 alone can be given by a substrate length L0 and the distance between a given illumination optical component 221, and its corresponding receiving optical component 222 can be given by the optical path length L3, which corresponds to the distance between the two components, with L3=L0+L1+L2. It is therefore understood that the substrate length L0 is taken in the direction between the two components 221, 222. In some embodiments, optical path length L3 between components 221, 222 is no greater than 140% of the substrate path length L0.

In some embodiments of the present invention the fiber optics component holder 223 is attached to the substrate holder 201 and may move together with it.

The light from illumination components 221 form probing beams 224, which probe the process region 207 and are collected by the receiving components 222. Receiving components 222 are again coupled into outgoing light fibers 220b, and exit the processing chamber 200 through the feedthrough 219. Outside the processing chamber the individual fibers 220a, 220b are bundled into cables 218a and 218b. Cables 218a are connected to component 217 of the light emission sub-module 211 and bundled cables 218b are connected to component 225 of the detection sub-module 212.

The entire system is controlled by the system computer 227. The processor associated with computer 227 sends operation instructions 228 to the optical processing module 210. The computer's processor may send process control instructions 229a to the processing chamber operator who then may take some action in response thereto, in a manual mode of operation. Alternatively, or in addition, the computer's processor may send process control instructions 229b to an electronic controller module 230 associated with the processing chamber, in an automated mode of operation.

In order to describe the system function, a brief theoretical background of the atomic spectroscopy measurement is given below.

The measured optical intensity at the detector when the probing beam is probing the process region in the vicinity of the element's emission/absorption spectral linewidth $I_{\delta\lambda}^{measured}$, is a combination of multiple factors and can be approximated as follows:

$$I_{\delta\lambda}^{measured} = I_{\delta\lambda}^{source} - L_{\delta\lambda}^{comp} + I_{\delta\lambda}^{spon.em.} - A_{\delta\lambda}^{el.} \quad (1)$$

$A_{\delta\lambda}^{el.}$ corresponds to the fraction of the illuminating light intensity, which is absorbed by the element particles in the atomic region probed by the light source, and generally is what one wishes to determine based on the observed intensity measurement $I_{\delta\lambda}^{measured}$.

$I_{\delta\lambda}^{source}$ is the intensity value of the probing light source. The probing light source may be an HCL source, which emits light at one or more element specific spectral linewidths $\delta\lambda$. Since the intensity of most commonly used element light sources tend to fluctuate during operation, constant referencing of $I_{\delta\lambda}^{source}$ is required.

$L_{\delta\lambda}^{comp}$ is the optical loss in the probing beam due to a variety of factors, such as potential overcoating of components 221 and 223 or component misalignment. One method of determining $L_{\delta\lambda}^{comp}$ is described with reference to FIG. 3. A second method of determining $L_{\delta\lambda}^{comp}$ is described with reference to FIGS. 4 and 5.

$I_{\delta\lambda}^{spon.em.}$ is the intensity value of the spontaneous atomic emission of the measured chemical element in the absence of any illumination by the probing beam. Many surface modification processes are associated with the generation or otherwise existence of energetic atomic particles in the process region 207 that have their own spontaneous atomic emission at the same spectral linewidth $\delta\lambda$ at which the absorption is measured. Therefore, the atomic particles that are being measured may have their own spontaneous atomic emission, which is independent of the emission in response to stimulation by a probing beam. $I_{\delta\lambda}^{spon.em.}$ is measured with $I_{\delta\lambda}^{source}$ being blocked or disabled. Although $I_{\delta\lambda}^{spon.em.}$ can often be relatively small compared to $I_{\delta\lambda}^{source}$, spontaneous atomic emission intensity varies from element to element and strongly depends on the process conditions and chamber geometries.

In one embodiment of the present invention, $I_{\delta\lambda}^{spon.em.}$ is measured during each measurement cycle in order to achieve better measurement accuracy of the atomic element concentration in the process region 207 and provide actionable information related to the process control.

In some embodiments of the present invention, multiple surface properties and process parameters are calculated by independently measuring or accounting for $I_{\delta\lambda}^{spon.em.}$. For example the plasma power of the particle source 203 can be correlated to the measured $I_{\delta\lambda}^{spon.em.}$ and used to control the processing conditions inside processing chamber 200. This is shown in FIG. 6b.

In some cases, $I_{\delta\lambda}^{spon.em.}$ is equal to zero; the particles in the process region 207 do not have spontaneous atomic emission and are excited to emit light only under illumination by the stimulating probing beam. In such cases, formula (1) is reduced to $$I_{\delta\lambda}^{measured} = I_{\delta\lambda}^{source} - L_{\delta\lambda}^{comp} - A_{\delta\lambda}^{el.} \quad (2)$$

However, it is generally understood that processes such as physical and chemical vapor deposition, ion etching, ion implantation and laser ablation will usually result in some degree of spontaneous atomic emission.

Thus, from equation (1) and from the Beer-Lambert Law, the atomic absorption term $A_{\delta\lambda}^{el.}$ can be defined as:

$$A_{\delta\lambda}^{el.} = I_{\delta\lambda}^{source} - L_{\delta\lambda}^{comp} + I_{\delta\lambda}^{spon.em.} - I_{\delta\lambda}^{measured} = \varepsilon_{\delta\lambda} \cdot C \cdot l \quad (3)$$

where $\varepsilon_{\delta\lambda}$ is the molar absorption coefficient of the measured chemical element in the spectral linewidth $\delta\lambda$, C is the molar concentration of the measured element, and l is the length of the absorbing zone within the atomic region directly facing the detector, respectively. In the embodiment presented in FIG. 2 the dimension l is equal to the distance L3 between components 221 and 222.

It can be seen from Eq. (3) that given an observed measurement $I_{\delta\lambda}^{measured}$, one may wish to compensate for any spontaneous atomic emission $I_{\delta\lambda}^{spon.em.}$, before determining atomic absorption $A_{\delta\lambda}^{el.}$, in addition to referencing the source intensity $I_{\delta\lambda}^{source}$ and optical loss $L_{\delta\lambda}^{comp}$.

For the purpose of the subject matter of the present application, $A_{\delta\lambda}^{el.}$ is proportional to the amount of the atomic particles. A plurality of atomic element concentration measurements taken during the course of processing a substrate surface can be used to determine a time-varying profile of amounts of at least one element of interest in the process region. The plurality of time-varying amounts of at least one element of interest in the process region can then be used to calculate various properties of the substrate surface being modified. Exemplary surface properties, which may be calculated using methods known to those skilled in art, include such things as the momentary mass and thickness of the deposited or etched material, deposition or etching rate, etching selectivity and profile, chemical composition, phase, crystal lattice and microstructure of a thin film being modified (deposited or removed) on a substrate surface via a vacuum-assisted process, as well as a variety of physical parameters of the modified surface such as structural, mechanical, chemical and thermal properties and others.

The amount of the atomic particles can also be used to control one or more of the processing conditions inside processing chamber 200. The processing conditions may include such things such as an operation setpoint of a particle source within the processing chamber, gas flow rates of the gases introduced into the processing chamber, a precursor gas conditions, a temperature setpoint inside the processing chamber, a pressure setpoint in the processing chamber, and a bias voltage applied to the components of the processing chamber.

Figure 6:
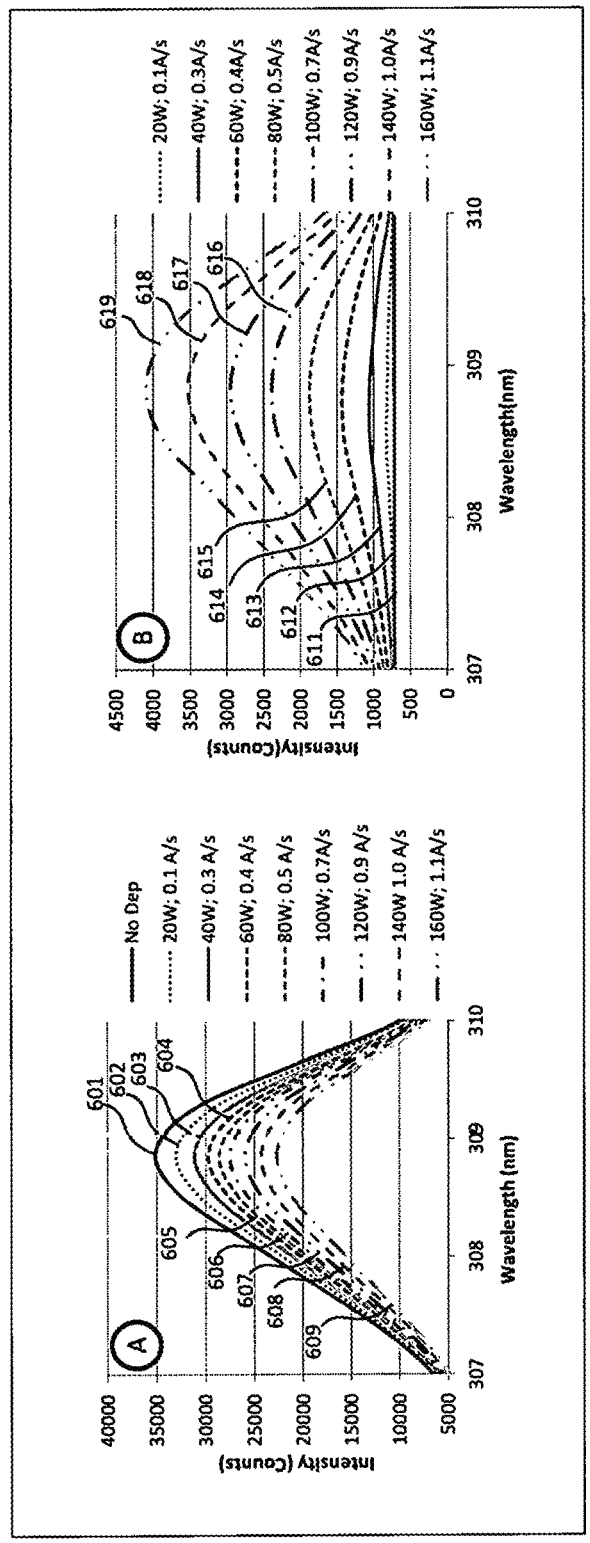
FIG. 6 shows an example of atomic absorption spectroscopy and the corresponding spontaneous atomic emission spectroscopy data as functions of the discharge power of a magnetron sputtering source during deposition of aluminum.

As an example of this, FIG. 6 shows the effect of changing the power applied to the particle source 203 on atomic absorption and emission values.

Figure 7:
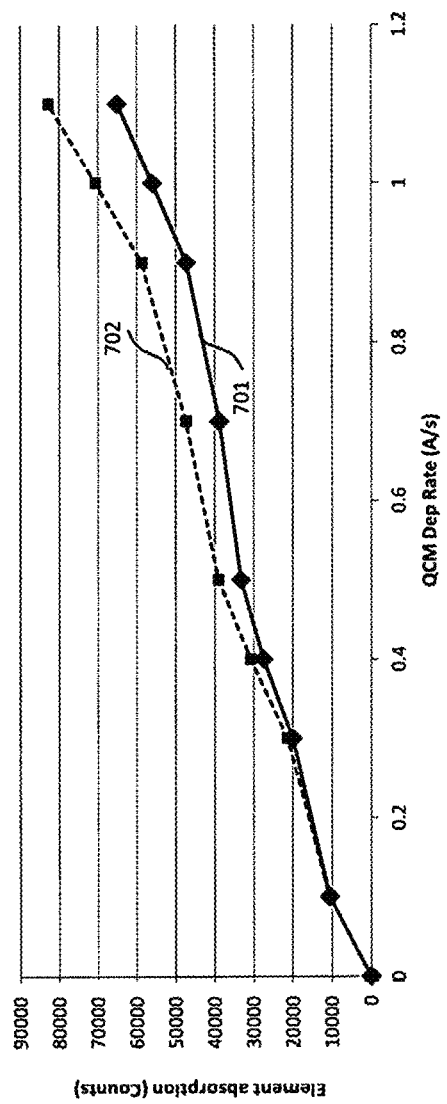
FIG. 7 depicts the measured aluminum element absorption, according to one embodiment of the present invention, as a function of the film deposition rate.

In one embodiment, $A_{\delta\lambda}^{el.}$ is correlated to the momentary deposition rate of the deposited element. This is illustrated in FIG. 7.

In another embodiment $A_{\delta\lambda}^{el.}$ is measured for more than one spectral linewidths W of the same atomic element of interest in the process region and is correlated to the amounts of particles of the same element having different energy and excitation states.

In another embodiment, $A_{\delta\lambda}^{el.}$ is measured for different atomic elements in the process region and the relative concentration of these elements is correlated to the chemical composition of the film deposited on the substrate. This is illustrated on FIG. 8.

In still another embodiment, $A_{\delta\lambda}^{el.}$ is measured for different atomic elements over a plurality of directions and/or locations in the process region and is correlated to the spatial uniformity of any of these surface properties or process parameters.

In yet another embodiment of the present invention $A_{\delta\lambda}^{el.}$ is measured for different atomic elements during a plurality of moments in the process region during the process and is correlated to the temporal uniformity or homogeneity of any of these surface properties in the duration of the process and in depth of the growing film.

Figure 1:
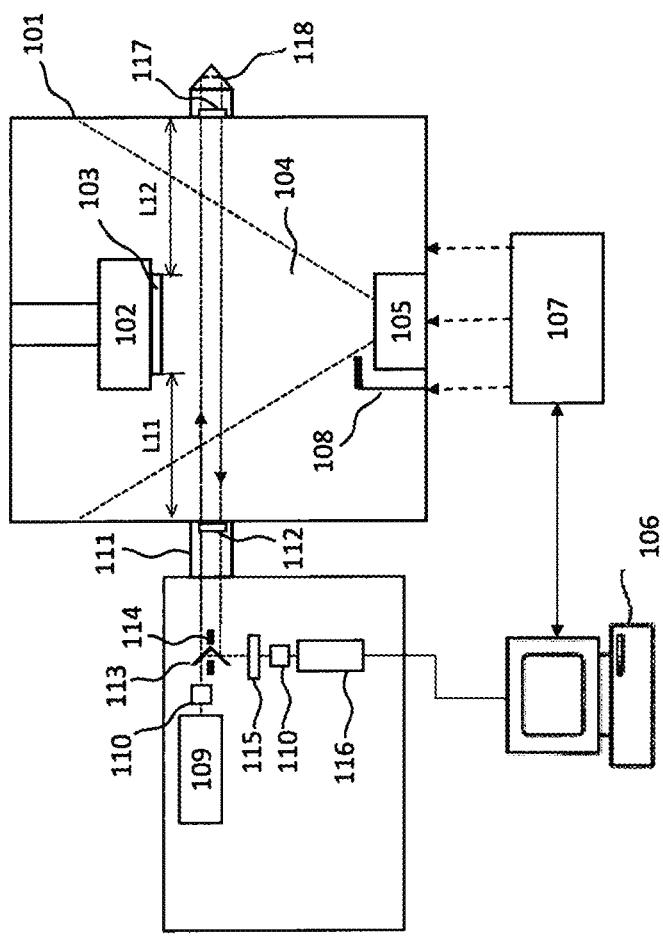
FIG. 1 is a functional block diagram of a prior art in-situ atomic absorption spectroscopy thin film process monitoring system.

A specific advantage of the disclosed invention is the fact that $A_{\delta\lambda}^{el.}$ can be measured only in the process region 207 in the immediate vicinity of the modified/deposited substrate (distance L3 in FIG. 2) and is proportional to the rate at which the substrate is modified/deposited. Another advantage is the ability to account for $I_{\delta\lambda}^{spon.em.}$, which is proportional to a plurality of process conditions such as particle source power, temperature, etc. These two advantages are associated with the fact that the measurement is performed between components 221 and 222 inside the process region 207 at distances L1, L2 and height H and is not affected by the interaction of the probing beam with the material that is spread in other areas of the processing chamber such as areas L1 and L2 of FIG. 1.

The operation of the system shown in FIG. 2 is explained with reference to a plurality of discrete measurement states, shown in FIG. 3. In particular, FIG. 3 shows six measurement states that the system may occupy. It is understood that in this embodiment, a single duty cycle for the system may comprise cycling through all six states. However, it is also possible to utilize the system using fewer than all six states in a single duty cycle, as well as enter these states in a different order.

Column 301 shows component settings for the first state ("State 1"), which corresponds to the detector's dark reference state $P_{\delta\lambda}^{detector}$, measured in the units of the detector. In the dark reference state, the system measures the noise of the detector 226, which depends on multiple factors such as detector type, temperature, etc. Component 225 is set to position "5" with a termination fiber, or closed by a shutter, which can be internal to the detector itself or a separate component (not shown in FIG. 2). Thus, in the first state, no light is allowed to enter the detector 226.

Column 302 shows component settings for the second state ("State 2"), which corresponds to a chamber background reference state $P_{\delta\lambda}^{background}$. The chamber background reference state may be used to reference the optical loss in the fiber-optics system and the light conditions inside the processing chamber 200 with respect to each of the measurement channels when no surface modification is being performed. The particle sources 203 and 204 are closed by shutters 208 and 209, and the light sources 213 are closed by shutters 214. However, the detector 226 is allowed to receive light. The optical switch (Component 225) switches between all the measurement channels (shown as Positions "1", "2', "3") and the detector 226 measures the light conditions at each of the measurement channels.

After states "1" and "2" are completed the computer takes the larger of the two values and sets it as a dark reference value $P_{\delta\lambda}^{dark}$, needed to calculate the light intensity values in unitless numbers from zero to one. Both values may also change during the process of system operation and at some conditions one may overcome the other; therefore, constant monitoring of both is recommended.

Column 303 shows component settings for the third state ("State 3"), which corresponds to a light sources reference state $P_{\delta\lambda}^{light}$. This state is used to reference the light power of the sources 213. Component 214 is configured such that all light sources (when more than one light source is used) can be coupled together, or referenced sequentially. Component 216 is switched to position "1" and component 225 to position "4". In this state, the light from the light sources is sent directly to the detector 226 without first passing through component 217, fiber optic cables 218 and the chamber 200, and the total power from the light source is measured.

Column 304 shows component settings for the fourth state ("State 4"), which corresponds to the spontaneous atomic emission measurement $P_{\delta\lambda}^{spon.em.}$. In this state, the particle sources 203, 204 are operating and the shutters 208 and 209 are open. Processing region 207 is active and the process of surface modification is taking place. Component 214 is closed and light from the light sources 213 does not probe the processing region 207. Component 225 switches between all measurement channels and detector 226 measures the signal from each of the channels with the sources 203, 204 and components 208 and 209 open. After the completion of measuring state 4, the value $I_{\delta\lambda}^{spon.em.}$ is calculated by the system computer 227 for each of the specific element particles that are measured in the processing region 207.

Column 305 shows component settings for the fifth state ("State 5"), which corresponds atomic absorption measurement $P_{\delta\lambda}^{at.abs.}$. In this state the sources 203, 204 are operating and the components 208 and 209 are open. Processing region 207 is active and the process of surface modification is taking place. Component 214 is open and light from the light sources 213 probes the processing region 207 via all measurement channels. Component 225 switches between all measurement channels and detector 226 measures the signal from each of the channels.

Parameters $P_{\delta\lambda}^{dark}$, $P_{\delta\lambda}^{light}$, $P_{\delta\lambda}^{spon.em.}$, $P_{\delta\lambda}^{at.abs.}$, measured during states "1" to "5" are the values measured at the detector 226. These can be digital counts number, light power or other units depending on the detector type. After completion of states "1" to "5" the intensity is normalized by the system computer 227 for each of the specific element particles that are measured in the processing region 207.

$$I_{\delta\lambda}^{measured} = \frac{P_{\delta\lambda}^{measured} - P_{\delta\lambda}^{dark}}{P_{\delta\lambda}^{light} - P_{\delta\lambda}^{dark}} \quad (4)$$

Some other calculations can also be performed, such as measuring system noise and its statistics and/or adjusting detector gain.

Column 306 shows component settings for the sixth state ("State 6"), which is used to account for potential contamination of the optical components' surfaces $L_{\delta\lambda}^{comp}$ during the operation of the system. In this state the shutters 208 and 209 are closed. Processing region 207 is not active and the process of surface modification is not taking place. Component 214 is open and light from the light sources 213 probes the processing region 207 via each of the measurement channels. Component 225 switches between each of the measurement channels and detector 226 measures the signal from each of the channels. The measured light intensity values are compared to the initial intensity values measured during State 3 before the process of surface modification has begun. The attenuation in the intensity values is attributed to contamination or overcoat of the optical components 221 and 222 and can be taken into account.

Figure 4:
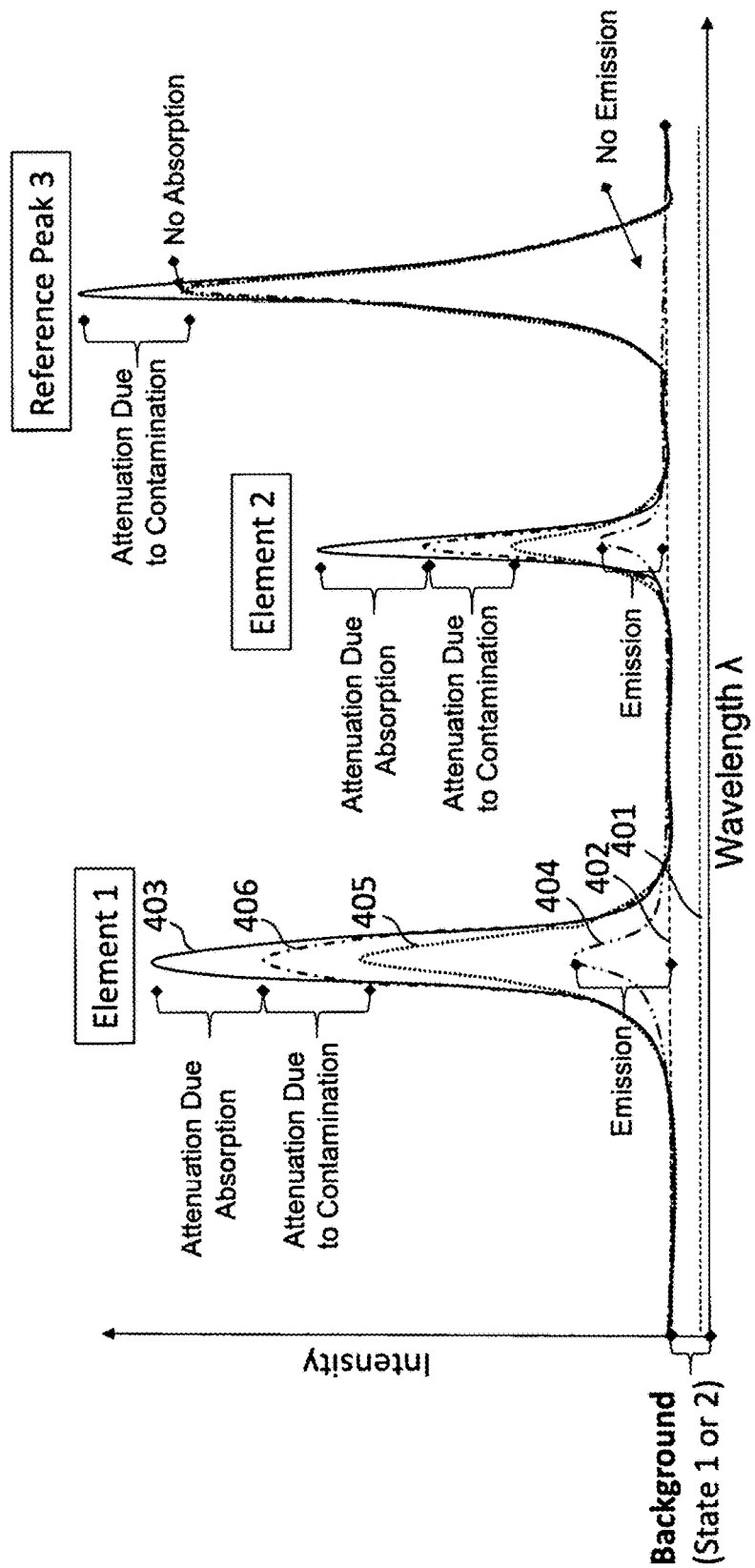
FIG. 4 shows exemplary spectra measured during the operation of the system shown in FIG. 2 and FIG. 3.

State 6 is included in FIG. 3 for clarity and completeness. Other methods for referencing the contamination of the optical surfaces inside the processing chamber $L_{\delta\lambda}^{comp}$ are also possible, as shown in FIG. 4. Alternatively, or additionally, more than one method can be used.

FIG. 4 represents exemplary spectra measured during the operation of the system. It shows four individual spectral curves and three corresponding emission lines. Element 1 and Element 2 are the emission lines of two individual atomic elements in the processing region 207. For example, one of the strongest absorption lines of the chemical element Silicon (e.g., "Element 1") is at 251.61 nm, while one of the strongest absorption lines of Aluminum (e.g., "Element 2") is at 309.27 nm.

Reference peak 3 is the emission line of the element that is used for reference of the component contamination $L_{\delta\lambda}^{comp}$, such as the emission line of the noble gas that is present in the HCL light sources 213. For example, HCL sources are frequently filled with Neon gas, having a strong emission peak at 352.05 nm. The reference peak 3 corresponds to an element that is not presented in the processing region 207. The intensity of reference peak 3 may change only due to factors that are dependent on the status of the measurement system, such as deposition of thin film on components 221 and 222 of the component holder 223, both of which may affect detected light intensities. Thus, reference peak 3 is used to determine the contamination level of components 221 and 222, by providing a correction factor.

Spectral curve 401 displays the detector "dark" reference, measured during State 1 (column 301 in the table of FIG. 3). It might, therefore, show some small non-zero detector signal level representing the noise of the detector.

Spectral curve 402 displays the chamber background reference, measured during State 2 (column 302 in the table of FIG. 3), and, therefore, represents the ambient signal received on the various measurement channels.

Spectral curve 403 shows the light source reference measured during State 3 (column 303 in the table of FIG. 3). The difference between the spectral curves 402 and 403 at any wavelength represents the value of $I_{\delta\lambda}^{source}$ at that wavelength.

Spectral curve 404 shows an optical emission measurement measured during State 4 (304 in FIG. 3). Element 1 and Element 2 display their specific atomic emission peaks. The intensity of each of these peaks is proportional to the concentration of element 1 and element 2 in the processing region 7. Thus, the intensity is dependent on the process parameters such as deposition or etching rate, particle source power, temperature and the like. There is no emission at the reference peak 3 since element 3 is not present in the region 207.

Curve 405 shows one specific atomic absorption curve measured during State 5 (column 305 in FIG. 3). Due to the absorption of photons by element 1 and element 2 as well as due to contamination of the optical components 221 and 222, all peaks 1, 2 and 3 display specific attenuation values. The attenuation value at reference peak 3 is used to correct the attenuation values at the peaks of element 1 and element 2. It can also be used to correct the emission values at the peaks of element 1 and 2 in curve 404. The result from the correction is the spectral curve 406, which displays the real attenuation of the element 1 and element 2 due solely to the atomic absorption $A_{\delta\lambda}^{el.}$ in the processing region 207.

Figure 5:
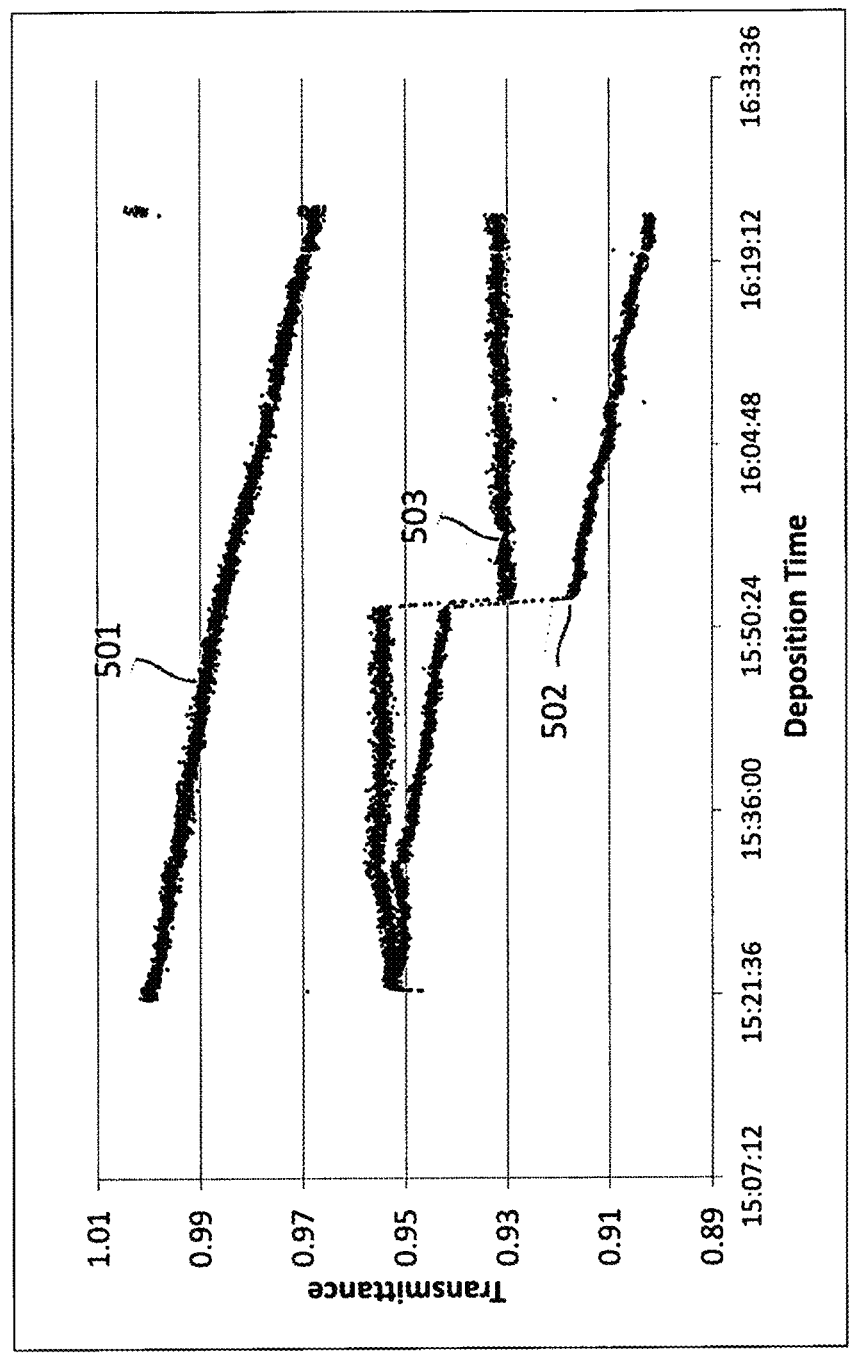
FIG. 5 shows one example of the in situ correction process of the emission values of Aluminum peak at 309.27 nm during thin film deposition using the attenuation of the Neon gas line at 352.05 nm.

FIG. 5 shows one example of the process of constant correction of the emission value of Aluminum peak at 309.27 nm during aluminum thin film deposition by magnetron sputtering. Curve 501 displays the transmittance of the probing beam at the emission peak of Neon gas in the HCL source at 352.05 nm. As the deposition takes place, the Ne peak attenuates proportionally to $L_{\delta\lambda}^{comp}$, reducing the probing beam transmittance, due to deposition of aluminum on the optical components. Attenuation is also observed in curve 502, which displays the transmittance of the probing beam at the emission line of Aluminum at 309.27 nm. Curve 503 is the Aluminum transmittance curve, corrected by accounting for 501 in 502.

Most chemical elements have multiple absorption lines with different strength (power), as well as some absorption lines may be represented as a superposition of more than one line. In addition, some absorption lines may be optically resolved as combination of two or more narrow individual lines with different strength, according to the state of the atomic particles in the processing region 207.

In some embodiments of the present invention specific features of the absorption lines are measured and monitored and may include integration, such as integration over one or more linewidths $\delta\lambda$, as well as more complex shape analysis.

In some embodiments of the present invention, more than one absorption line of the same element is measured simultaneously and may include monitoring the ratios between the values of the individual absorption lines.

Yet, in other embodiments, the same multi-line monitoring is carried out for multiple elements simultaneously and may include monitoring the ratios between the values of the individual absorption lines.

FIG. 6 shows an example of atomic absorption spectroscopy data (marked as A) and the corresponding spontaneous atomic emission spectroscopy data (marked as B) as functions of the discharge power of a magnetron sputtering source during deposition of aluminum. Curves 601 to 609 show the measured optical spectrum within $\delta\lambda=307$-310 nm, corresponding to the element absorption line of aluminum, for different discharge power of the magnetron sputtering source. Curve 601 shows the maximum signal intensity, measured when no deposition occurs on the substrate, while curves 602-609 show the signal intensity when the discharge power increases from 20 Watts up to 160 Watts, respectively. The deposition rate is also shown at each discharge power value.

Curves 611 to 619 show the corresponding intensity of the aluminum spontaneous atomic emission as functions of the discharge power of the magnetron sputtering source during the deposition of aluminum. Curve 611 corresponds to curve 601 as no deposition on the substrate occurs. Curve 612-619 correspond to curves 602-609, respectively, as the discharge power increases from 20 Watt to 160 Watt.

FIG. 7 depicts the measured aluminum element absorption according to one embodiment of the present invention, as a function of the film deposition rate, measured independently by a quartz crystal monitor (QCM). Curve 701 shows the measured aluminum element absorption without taking into account the spontaneous atomic emission from aluminum particles. Curve 702 shows the aluminum element absorption calculated after taking into account the spontaneous atomic emission from aluminum particles.

Figure 8:
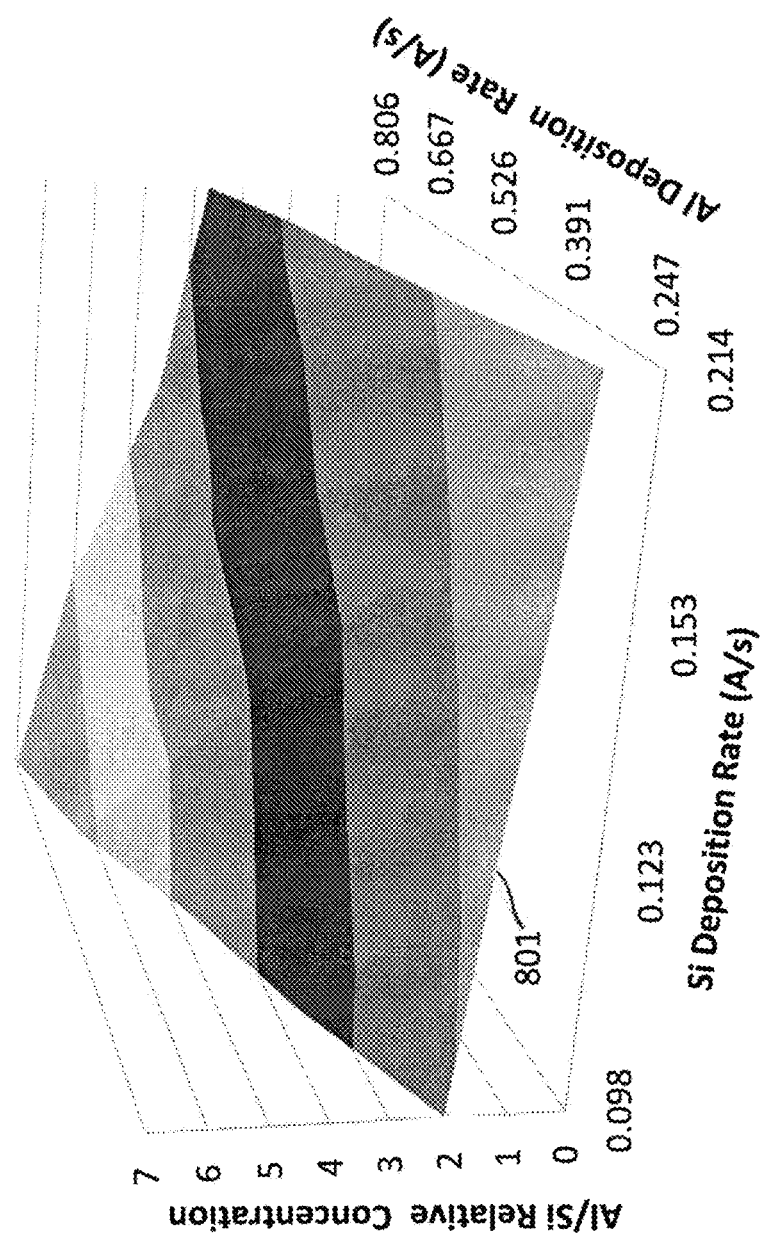
FIG. 8 shows a 3D plot of the relative concentration of aluminum and silicon Al/Si during co-sputtering as a function of the deposition rate of aluminum and the deposition rate of silicon used for monitoring chemical composition of the thin film.

FIG. 8 shows a 3D plot of the relative concentration of aluminum and silicon Al/Si during co-sputtering as a function of the deposition rate of aluminum and the deposition rate of silicon. Plot 801 of FIG. 8 can be used to determine the chemical composition of the resulting film on the substrate during the process of film deposition.

Figure 9:
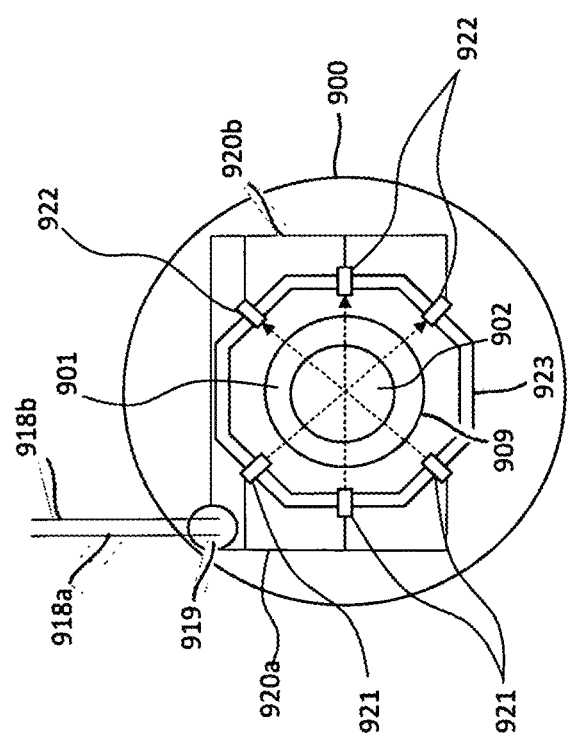
FIG. 9 illustrates one embodiment of the fiber optics component holder 223 seen in FIG. 2.

FIG. 9 illustrates one embodiment of the fiber optics component holder 923, represented on FIG. 2 by reference character 223. It represents a plan view of the component holder 923 and substrate 902, seen in a bottom-up view of the processing chamber ceiling 900. The chamber ceiling supports one or more fiber optics feedthroughs 919, represented as 219 on FIG. 2. The fiber optics component holder 923 is installed inside the processing chamber in the area surrounding the substrate holder 901 without touching the substrates 902. Optical fibers 918a and 918b enter the processing chamber through the feedthrough 919 and are connected to illumination and receiving components 921 and 922 by using incoming fibers 920a and outgoing fibers 920b, respectively. Components 921 and 922 are arranged in a configuration such that the probing beams are not parallel to each other, but rather intersect one another in the shown bottom-up view of FIG. 9.

In some embodiments, components 921 and 922 may be positioned such that the probing beams do not intersect each other. For example, pairs of components 921, 922 may be positioned at slightly different heights relative to the substrate 902. Alternatively, the components 921 and components 922 are positioned such that the probing beams are parallel to one another in the same plane or in different planes (in which case they are not parallel in 3D space).

Figure 10:
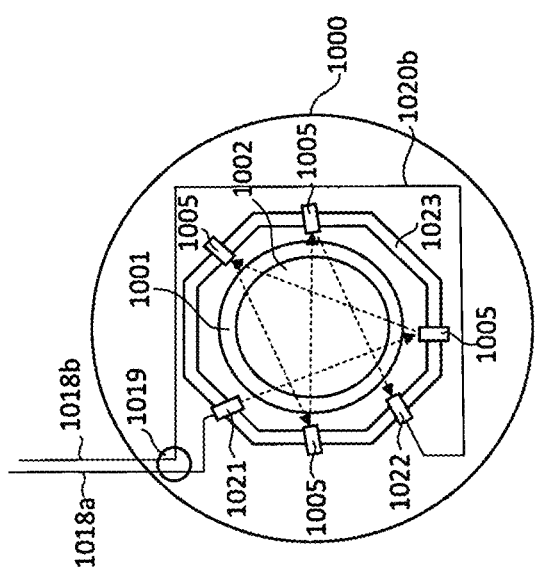
FIG. 10 shows a second embodiment of the fiber optics component holder 223 seen in FIG. 2.

FIG. 10 illustrates one embodiment of the fiber optics component holder 1023, represented on FIG. 2 by reference character 223 and on FIG. 9 as reference number 923. It represents a plan view of the component holder 1023 and substrate 1002, seen in a bottom-up view of the ceiling of processing chamber 1000. The chamber 1000 supports one or more fiber optics feedthroughs 1019. The fiber optics component holder 1023 is installed inside the processing chamber in the area surrounding the substrate holder 1001 without touching the substrates 1002. Optical fibers 1018a enter the processing chamber through the feedthrough 1019 and are connected to the illumination component 1021. Component 1021 sends a probing beam to one or more reflective components 1005 such as mirrors (4 are shown) before it reaches receiving component 1022. Fibers 1020b are connected to the receiving component 1022 and exit the chamber 1000 through feedthrough 1019 and exit fiber cables 1018b.

In the embodiment of FIG. 10, components 1021, 1022 and 1005 are arranged in a configuration such that the probing beam intersects itself as it reflects from one component 1005 to another.

However, in other embodiments, components 1005 may be positioned such that the probing beam goes back and forth from one reflective component 1005 to another without intersecting within the area occupied by the substrate 1002.

In yet other embodiments the probing beam may intersect within the substrate area, but not in the same plane.

In still other embodiments, the reflective components 1005 may combine other functions simultaneously with the reflective function, such as light polarization, depolarization, beam shaping, filtering, focusing, etc.

Figure 11:
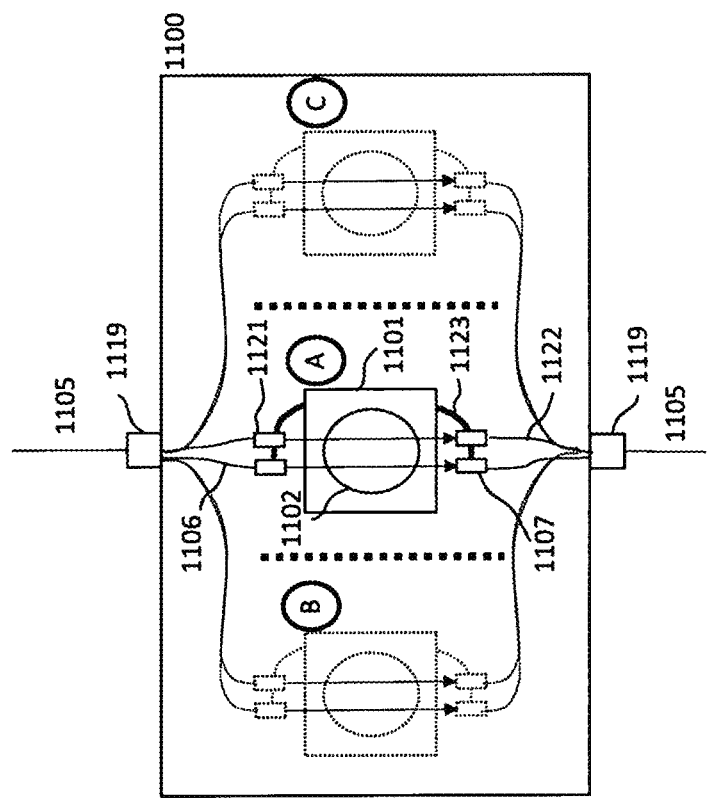
FIG. 11 shows a view of processing equipment, where the substrate holder performs translational movement in one or separate chambers or chamber compartments.

FIG. 11 represents another plan view of a component holder 1123 and substrate holder 1101 within a processing chamber 1100. In the embodiment of FIG. 11, the substrate holder 1102 together with the substrate 1102 are configured to undergo translational movement within the processing equipment such as by moving into separate process areas A, B and C. Process areas A, B, and C may be just areas where different stages of the same process or different processes occur in the same processing chamber. They may also be physically separated as individual compartments A, B and C of the same processing chamber.

In some embodiments, each compartment is provided with its own component holder 1123, which remains in place as the substrate holder 1101 moves. In other embodiments, the substrate holder 1101 and its corresponding component holder 1123 move together from process area to process area and/or from compartment to compartment. In still other embodiments, such as in a cluster tool, the substrate holder 1101 and its corresponding component holder 1123 may move from processing chamber to processing chamber through interconnecting valves or loadlocks.

Persons skilled in the art would recognize that a variety of surface processing equipment exists where the substrate holders are transferred from one part or compartment of the chamber to another, or from one chamber to another chamber in a line deposition configuration.

The chamber or the separate compartments support one or more fiber optics feedthroughs 1119. Separate fiber optics component holders 1123 are installed inside each of the compartments for monitoring the ongoing process. Each component holder 1123 supports one or more illumination and/or receiving components and/or reflective components, showing generally as optical components 1121, and 1122 connected to the fiber optics feedthroughs 1119 by fibers or fiber cables. Thus, for example, a first component holder may hold two or more illumination components on one side of a substrate while a second component holder may hold two or more receiving components on the opposite side of the substrate. Other combinations mixing and matching these components on a given component holder and/or a plurality of component holders associated with a single substrate holder and/or substrate are also envisioned.

According to another embodiment of the present invention the component holder 1123 is attached to the substrate holder 1101 and moves together with it.

Figure 12:
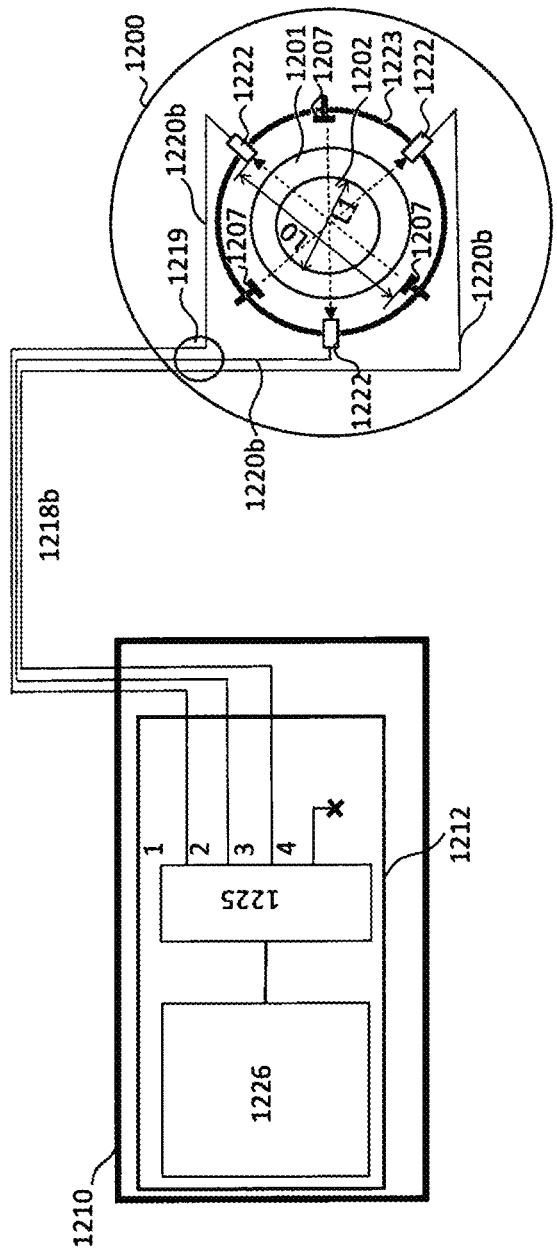
FIG. 12 shows a functional block diagram of a second embodiment of a system in accordance with the current invention, configured to measure only spontaneous atomic emission.

FIG. 12 shows a functional block diagram of another embodiment of a system in accordance with the current invention, configured to measure only the spontaneous atomic emission of the particles in the process region 207. For simplicity only the processing chamber 1200 together with the substrate holder 1201, the substrate 1202 and the chamber feedthrough 1219 are shown. Although not specifically shown in FIG. 12, a person skilled in the art would recognize that all major elements of the system as shown in FIG. 2 would also be present in FIG. 12 in one form or another, such as particle sources 203, processing region 207, etc.

The component holder 1223 is installed in the vicinity of the substrate 1202 and holds several receiving components 1222 (3 are shown). In order to obstruct the view of the receiving components 1222 in a way that only light emitted from within the process region is accepted, light blocking components 1207 are positioned and aligned diametrically across the process region from each of the receiving components 1222. The distance between receiving components 1222 and blocking components 1207 is shown (in FIG. 2) as L0 and the diameter of the substrate area or area of interest is shown as L1.

According to some embodiments of the present invention the dimension L0 is no larger than 140% of the dimension L1.

According to still other embodiments of the present invention, receiving components 1222 are arranged as shown in FIG. 9, so that a given receiving component 1222 blocks the view of another receiving component 1222 that is positioned on the other side of the substrate. In such an embodiment, components 1222 are configured to operate as both receiving and light blocking component, as needed.

Multiple other configurations are also possible such as the ones shown in FIGS. 9, 10 and 11.

Receiving components 1222 are connected by fibers or fiber bundles 1220*b*, which exit the processing chamber 1200 through fiber optics feedthrough 1219. Components 1220 collect the spontaneous atomic emission of particles in the plasma region, which can be represented as proportional to the concentration of the emitting particles in the processing region.

Fibers 1218*b* are combined outside the processing chamber into a fiber optics cable 1218*b* and enter the optical processing module 1210, shown in FIG. 2 as position 210. In this case, only the detector sub-module 1212 is included, as no light source sub-module 211 is needed. Also, since there is no need of light source reference, the fiber-optics distribution component 1225 can be a 1×4 fiber optics switch, switching between the individual fibers marked as positions "1" to "3" and the detector dark reference position "4". Component 1225 is connected to the optical detector component 1226.

While the above discussion describes an entire processing system and/or processing method, it is contemplated that existing processing chambers may be modified to have features disclosed herein.

To modify an existing processing chamber, an assembly of components and computer software for their operation, or "kit" may be provided. Such a kit may include the optical processing module, the transmitting and receiving optical components, optical fibers and software to perform the necessary control, measurements, illumination and detection operations. A fiber optic component holder may also be included in such a kit.

To modify an existing processing chamber, one must install at least one illuminating optical component in the processing chamber, the at least one illuminating optical component being connected via optical fiber to the light emission sub-module; install at least one receiving optical component in the processing chamber, the at least one receiving optical component being connected via optical fiber to the optical detection sub-module; and installing software on a computer coupled to the optical processing module. The software, when installed, would (a) cause the light emission sub-module to output a generated light signal; (b) cause the optical detection sub-module to detect a resultant light signal in response to the generated light signal, the resultant light signal being reflective of an amount of atomic absorption by at least one element of interest in the process region; and (c) based on the resultant light signal, determine an amount of said at least one atomic element of interest in the process region.

It is understood that the foregoing prefer embodiments are only exemplary and the subject matter of the present application is not limited thereto.

What is claimed is:

1. A processing system comprising a processing chamber (200, 900, 1000, 1100, 1200) having a substrate holder (201, 901, 1001, 1101, 1201) for holding at least one substrate (202, 902, 1002, 1102, 1202) and a process region (207), the processing system configured to monitor and/or control a modification process occurring on the substrate, the processing system further comprising:
    at least one illuminating optical component (221, 921, 1021, 1121) mounted within the processing chamber and configured to receive at least one generated light signal comprising at least one element-specific spectral linewidth corresponding to at least one atomic element of interest, and direct at least one probing beam through the process region without intersecting the substrate, in response thereto;
    at least one corresponding receiving optical component (222, 922, 1022, 1122, 1222) mounted within the processing chamber and configured to receive said at least one probing beam after it has passed through the process region, and output at least one resultant light signal in response thereto, the at least one resultant light signal being reflective of an amount of atomic absorption by said at least one atomic element of interest in the process region, in response to said at least one element-specific spectral linewidth of the generated light signal;
    an optical processing module (210, 1210) comprising:
        a light emission sub-module (211) configured to output the at least one generated light signal, which is received by said at least one illuminating optical component; and
        an optical detection sub-module (212, 1212) configured to receive said at least one resultant light signal from the at least one receiving optical component;
    a processor (227, 230) coupled to at least the optical detection submodule and configured to determine, based on said at least one resultant light signal, an amount of said at least one atomic element of interest in the process region.

2. The processing system according to claim 1, wherein:
the at least one resultant light signal is reflective of a combined amount of atomic absorption and spontaneous atomic emission; and
the processor is configured to compensate for a spontaneous atomic emission component of the resultant light signal, when determining said amount.

3. The processing system according to claim 1, wherein:
a first distance L1 between the illuminating optical component and a first edge of the substrate is less than 50 mm;
a second distance L2 between the receiving optical component and a second edge of the substrate is less than 50 mm; and
a height H separating the probing beam from the substrate, is less than 30 mm.

4. The processing system according to claim 1, further comprising:
at least one reflective component (1005) positioned within the processing chamber to reflect the probing beam after it has passed through the process region, such that the probing beam passes a second time through the process region prior to being received by a receiving component and the at least one resultant light signal being outputted.

5. The processing system according to claim 1, wherein:
a plurality of atomic elements of interest are present in the process region;
the light emission submodule is configured to generate a plurality of element-specific spectral linewidths, with at least one element-specific spectral linewidth corresponding to each of said plurality of elements of interest;
the at least one resultant light signal comprises spectral information corresponding to said plurality of element-specific spectral linewidths; and
the processor is configured to determine an amount of each of said plurality of elements of interest present in the process region.

6. The processing system according to claim 1, wherein:
the light emission sub-module is configured to generate a plurality of element-specific spectral linewidths for a single atomic element of interest present in the process region;
the at least one resultant light signal comprises spectral information corresponding to said plurality of element-specific spectral linewidths for that single atomic element; and
the processor is configured to determine an amount of said single atomic element of interest in the process region, based on spectral information corresponding to said plurality of element-specific spectral linewidths.

7. The processing system according to claim 1, wherein:
the processor is configured to determine a plurality of amounts of said at least one atomic element of interest in the process region over time, and
based on said plurality of amounts, the processor is further configured to control at least one processing condition of the processing chamber, the at least one processing condition being one or more of an operation setpoint of a particle source (203, 204) in the processing chamber, gas flow rates of the gases introduced into the processing chamber, a precursor gas conditions, a temperature setpoint inside the processing chamber, a pressure setpoint in the processing chamber, and a bias voltage applied to the components of the processing chamber.

8. The processing system according to claim 1, further comprising:
at least one fiber optic component holder (FOCH) (223, 923, 1023, 1123, 1223) mounted within the processing chamber; wherein:
the illuminating optical component and its corresponding receiving optical component are both mounted on said at least one fiber optic component holder.

9. The processing system according to claim 8, wherein:
the processing chamber comprises a plurality of chamber compartments or process areas, at least two of the chamber compartments or process areas having at least one FOCH located therein; and
the substrate holder is configured to undergo translational movement in the processing chamber and enter different chamber compartments or process areas.

10. The processing system according to claim 1, wherein:
the processor is configured to determine a plurality of amounts of said at least one atomic element of interest in the process region over time; and
based on said plurality of amounts, the processor is further configured to determine one or more of a momentary mass, a momentary thickness, a deposition rate, an etching rate, an etching selectivity, an etching profile, a chemical composition, a phase, a crystal lattice and a microstructure of a thin film being modified on the substrate surface.

11. The processing system according to claim 10, wherein the processor is further configured to:
direct a plurality of probing beams to pass through different portions of said process region, to thereby form a corresponding plurality of resultant light signals; and
based on said corresponding plurality of resultant light signals, determine a spatial distribution of at least one of said momentary thickness, said deposition rate, said etching rate, said etching selectivity, said etching profile, said chemical composition, said phase, said crystal lattice and said microstructure of a thin film being modified on the substrate surface.

12. A method for in-situ monitoring and/or control of a surface modification process occurring on a substrate (202, 902, 1002, 1102, 1202) in a processing chamber (200, 900, 1000, 1100, 1200), the processing chamber having a particle source (203, 204) therein and a process region (207) between the particle source and the substrate, the method comprising:
providing a generated light signal comprising at least one element-specific spectral linewidth corresponding to at least one atomic element of interest into the processing chamber, via a first fiber optic cable extending from outside the processing chamber to inside the processing chamber;
based on the generated light signal, directing at least one probing beam through the process region, without intersecting the substrate;
receiving said at least one probing beam within the processing chamber after it has passed through said process region;
in response to receiving said at least one probing beam, outputting at least one resultant light signal via a second fiber optic cable extending from inside the processing chamber to outside the processing chamber, the at least one resultant light signal being reflective of an amount of atomic absorption by said at least one atomic element of interest in the process region, in response to said at least one element-specific spectral linewidth of the generated light signal; and based on the at least one resultant light signal, determining an amount of said at least one atomic element of interest in the process region.

13. The method according to claim 12, wherein:

the at least one resultant light signal is reflective of a combined amount of atomic absorption and spontaneous atomic emission; and the method further comprises:

compensating for a spontaneous atomic emission component of the resultant light signal, when determining said amount.

14. The method according to claim 12, wherein:

an optical path length L3 of the probing beam between said directing step and said receiving step, is no greater than 140% of a substrate length L0 measured in the direction traveled by the probing beam.

15. The method according to claim 12, comprising:

reflecting the probing beam at least once after it has passed through said process region, such that the probing beam passes through a different portion of said process region prior to being received and the at least one resultant light signal being outputted.

16. The method according any claim 12, comprising:

providing a generated light signal comprising a plurality of element-specific spectral linewidths, each spectral linewidth corresponding to a specific absorption peak of a single atomic element of interest;

generating a resultant light signal comprising a corresponding plurality of element-specific spectral linewidths; and determining an amount of said single atomic element of interest in the process region, based on spectral information corresponding to said plurality of element-specific spectral linewidths.

17. The method according to claim 12, wherein a plurality of atomic elements of interest are present in the process region; the method comprising:

providing a generated light signal comprising a plurality of element-specific spectral linewidths, each element-specific spectral linewidth corresponding to a single absorption peak of each of a corresponding plurality of different atomic elements of interest;

generating a resultant light signal comprising a corresponding plurality of element-specific spectral linewidths; and determining an amount of each of said plurality of elements of interest present in the process region.

18. The method according to claim 12, comprising:

determining a plurality of amounts of said at least one atomic element of interest in the process region over time; and based on said plurality of determined amounts, controlling at least one processing condition of the processing chamber, the at least one processing condition being one or more of an operation setpoint applied to a particle source within the processing chamber, gas flow rates of the gases introduced into the processing chamber, a precursor gas conditions, a temperature setpoint inside the processing chamber, a pressure setpoint in the processing chamber, and a bias voltage applied to the components of the processing chamber.

19. The method according to claim 12, comprising:

determining a plurality of amounts of said at least one atomic element of interest in the process region over time; and based on said plurality of determined amounts, determining one or more of a momentary mass, a momentary thickness, a deposition rate, an etching rate, an etching selectivity, an etching profile, a chemical composition, a phase, a crystal lattice and a microstructure of a thin film being modified on the substrate surface.

20. The method according to claim 19, comprising:

based on the generated light signal, directing a plurality of probing beams to pass through different portions of said process region, to thereby form a corresponding plurality of resultant light signals; and based on said plurality of resultant light signals passing through different portions of said process region, determining a spatial distribution of at least one of said momentary thickness, said deposition rate, said etching rate, said etching selectivity, said etching profile, said chemical composition, said phase, said crystal lattice and said microstructure of a thin film being modified on the substrate surface.

21. An in-situ monitoring kit for modifying a processing chamber (200, 900, 1000, 1100, 1200) of the sort configured to carry out a surface modification process on a substrate (202, 902, 1002, 1102, 1202) located therein, so that an amount of at least one element of interest within a process region (207) within the chamber can be determined using optical components mounted within the chamber itself, the kit comprising:

an optical processing module (210, 1210) comprising a light emission sub-module (211) and an optical detection sub-module (212, 1212);

at least one illuminating optical component (221, 921, 1021, 1121) for installation inside the processing chamber;

a first optical fiber to connect the optical processing sub-module to the at least one illuminating optical component, when the illuminating optical component is installed inside the processing chamber;

at least one receiving optical component (222, 922, 1022, 1122, 1222) for installation inside the processing chamber;

a second optical fiber to connect the optical processing sub-module to the at least one receiving optical component, when the receiving optical component is installed inside the processing chamber; and software, which when executed on a processor (227, 230) coupled to the optical processing module, is configured to:

cause the light emission sub-module to output a generated light signal;

cause the optical detection sub-module to detect a resultant light signal in response to the generated light signal, the resultant light signal being reflective of an amount of atomic absorption by at least one element of interest in the process region; and based on said resultant light signal, determine an amount of said at least one atomic element of interest in the process region.

22. The in-situ monitoring kit according to claim 21, wherein the software, when executed, is further configured to:

compensate for a spontaneous atomic emission component of the resultant light signal, when determining said amount.

23. The in-situ monitoring kit according to claim 21, further comprising:
a fiber optic component holder (FOCH) (223, 923, 1023, 1123, 1223) having the least one illuminating optical component mounted on a first portion thereof, and having the at least one receiving optical component mounted on a second portion thereof, wherein:
the receiving optical component is optically aligned with the illuminating optical component and spaced apart therefrom by an optical path length L3.

24. The in-situ monitoring kit according to claim 21, wherein the software, when executed, is further configured to:
determine a plurality of amounts of said at least one atomic element of interest in the process region over time; and
based on said plurality of amounts, control at least one processing condition of the processing chamber, the at least one processing condition being one or more of an operation setpoint applied to a particle source (203, 204) within the processing chamber, gas flow rates of the gases introduced into the processing chamber, a precursor gas conditions, a temperature setpoint inside the processing chamber, a pressure setpoint in the processing chamber, and a bias voltage applied to the components of the processing chamber.

25. The in-situ monitoring kit according to claim 21, wherein the software, when executed, is further configured to:
determine a plurality of amounts of said at least one atomic element of interest in the process region over time; and
based on said plurality of amounts, determine one or more of a momentary mass, a momentary thickness, a deposition rate, an etching rate, an etching selectivity, an etching profile, a chemical composition, a phase, a crystal lattice and a microstructure of a thin film being modified on the substrate surface.

26. The in-situ monitoring kit according to claim 25, wherein the software, when executed, is further configured to:
direct a plurality of probing beams to pass through different portions of said process region, to thereby form a corresponding plurality of resultant light signals; and
determine a spatial distribution of at least one of said momentary thickness, said deposition rate, said etching rate, said etching selectivity, said etching profile, said chemical composition, said phase, said crystal lattice and said microstructure of a thin film being modified on the substrate surface.

* * * * *